US011365257B2

(12) United States Patent
Chiffoleau et al.

(10) Patent No.: US 11,365,257 B2
(45) Date of Patent: Jun. 21, 2022

(54) METHODS FOR PROMOTING T CELLS RESPONSE BY ADMINISTERING AN ANTAGONIST OF HUMAN C-TYPE LECTIN-LIKE RECEPTOR 1 (CLEC-1)

(71) Applicants: INSERM (INSTITUT NATIONAL DE LA SANTÉ ET DE LA RECHERCHE MÉDICALE), Paris (FR); UNIVERSITÉ DE NANTES, Nantes (FR); OSE IMMUNOTHERAPEUTICS, Nantes (FR)

(72) Inventors: Elise Chiffoleau, Nantes (FR); Géraldine Teppaz, St. Herblain (FR); Nicolas Poirier, Treillieres (FR); Bernard Vanhove, Rezé (FR); Vanessa Gauttier, Rezé (FR)

(73) Assignees: INSERM (INSTITUT NATIONAL DE LA SANTE ET DE LA RECHERCHE MEDICALE), Paris (FR); UNIVERSITE DE NANTES, Nantes (FR); OSE IMMUNOTHERAPEUTICS, Nantes (FR)

( * ) Notice: Subject to any disclaimer, the term of this patent is extended or adjusted under 35 U.S.C. 154(b) by 352 days.

(21) Appl. No.: 16/343,757

(22) PCT Filed: Oct. 20, 2017

(86) PCT No.: PCT/EP2017/076911
§ 371 (c)(1),
(2) Date: Apr. 20, 2019

(87) PCT Pub. No.: WO2018/073440
PCT Pub. Date: Apr. 26, 2018

(65) Prior Publication Data
US 2019/0309075 A1 Oct. 10, 2019

(30) Foreign Application Priority Data

Oct. 21, 2016 (EP) .................................... 16306381
Jul. 24, 2017 (EP) .................................... 17305988

(51) Int. Cl.
*A61P 35/00* (2006.01)
*C07K 14/47* (2006.01)
*C12N 15/115* (2010.01)
*C07K 16/28* (2006.01)

(52) U.S. Cl.
CPC .......... *C07K 16/2851* (2013.01); *A61P 35/00* (2018.01); *C07K 14/4726* (2013.01); *C12N 15/115* (2013.01); *C07K 2317/732* (2013.01); *C07K 2317/76* (2013.01); *C07K 2319/30* (2013.01)

(58) Field of Classification Search
CPC .... A61P 35/00; C07K 14/4726; C12N 15/115
See application file for complete search history.

(56) References Cited

U.S. PATENT DOCUMENTS 8,246,959 B1    8/2012  Clark

OTHER PUBLICATIONS

P. Thebault et al., "The C-Type Lectin-Like Receptor CLEC-1, Expressed by Myeloid Cells and Endothelial Cells, is Up-Regulated by Immunoregulatory Mediators and Moderates T Cell Activation", The Journal of Immunology,vol. 183, No. 5, Sep. 1, 2009 (Sep. 1, 2009), p. 3099-3108.
Plato Anthony et al., "C-type lectin-like receptors of the dectin-1 cluster: ligands and signaling pathways.", International Reviews of Immunology Apr. 2013,vol. 32, No. 2, Apr. 2013 (Apr. 2013), p. 134-156.
M. Eriksson et al., "Abstract 121. Targeting C-type lectin receptors with synthetic carbohydrates to modulate mmune responses", Glycoconjugate Journal,vol. 28, No. 5, Jan. 1, 2011 (Jan. 1, 2011), p. 245-246.

*Primary Examiner* — Robert S Landsman
(74) *Attorney, Agent, or Firm* — Arrigo, Lee, Guttman & Mouta-Bellum LLP

(57) ABSTRACT

The present invention relates to methods for promoting T cells response. The inventors examined the expression and function of CLEC-1 in human DCs and demonstrated for the first time a cell-surface expression. They investigated its functional role following triggering on orchestration of T-cell responses. The inventors showed in vitro and in vivo with CLEC-1 deficient rats and rat CLEC-1 Fc fusion protein that disruption of CLEC-1 signalling enhances in vitro Th17 activation and in vivo enhances T cell priming and Th17 and Th1 activation. In particular, the present invention relates to CLEC-1 antagonists for promoting T cells response in a subject in need thereof.

10 Claims, 20 Drawing Sheets

Figure 1A:
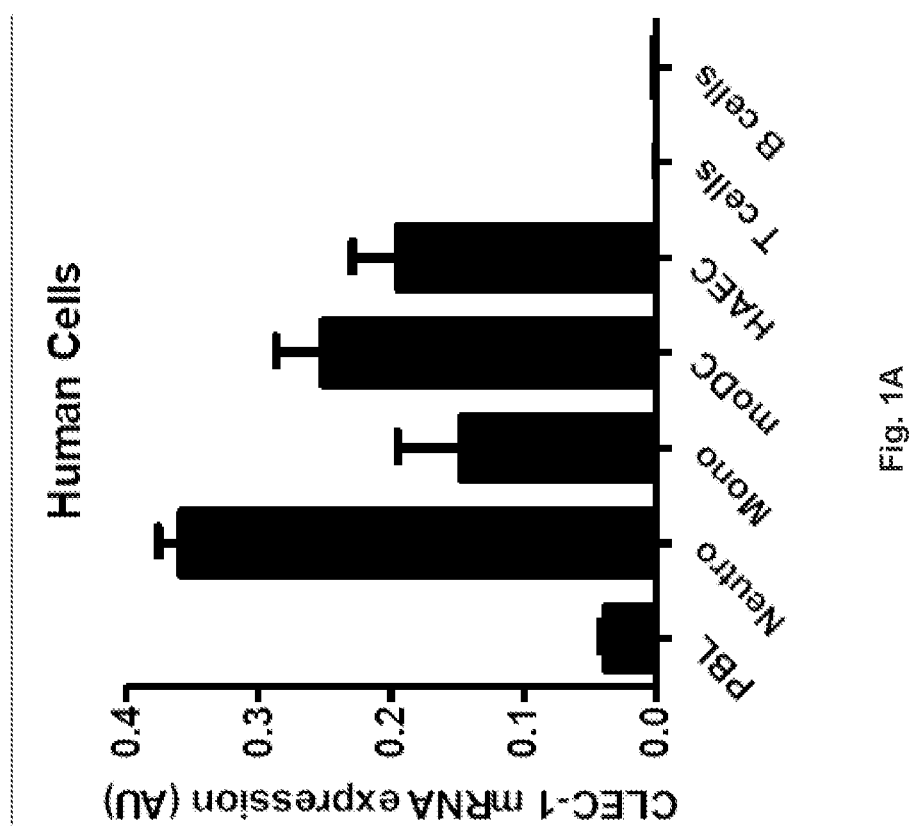

Specification includes a Sequence Listing.

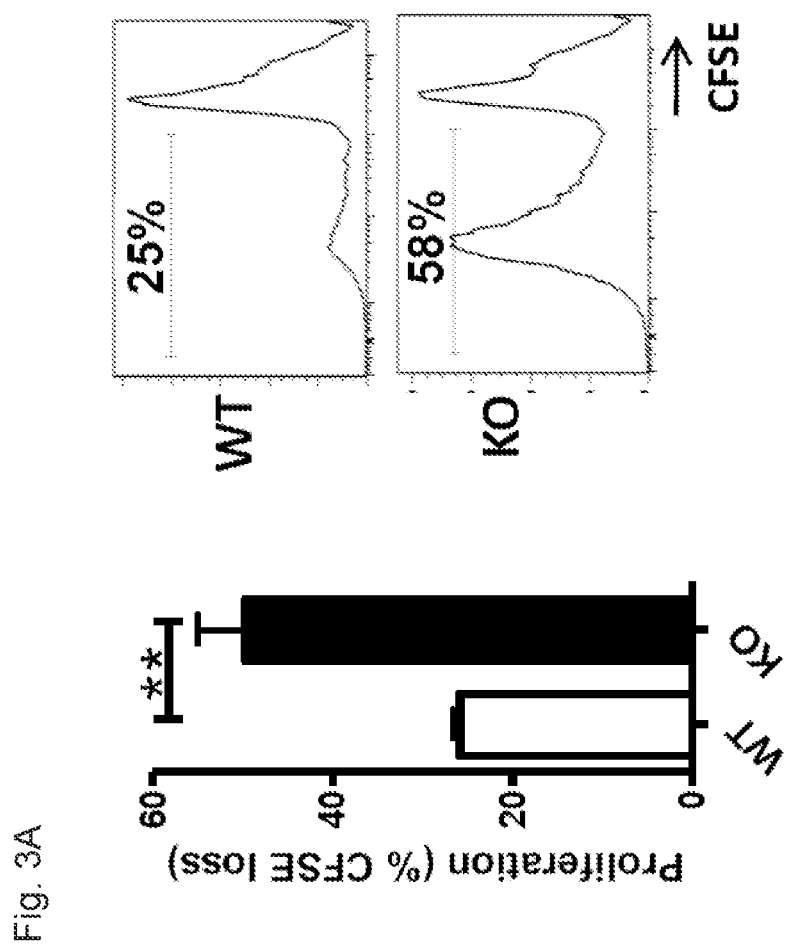

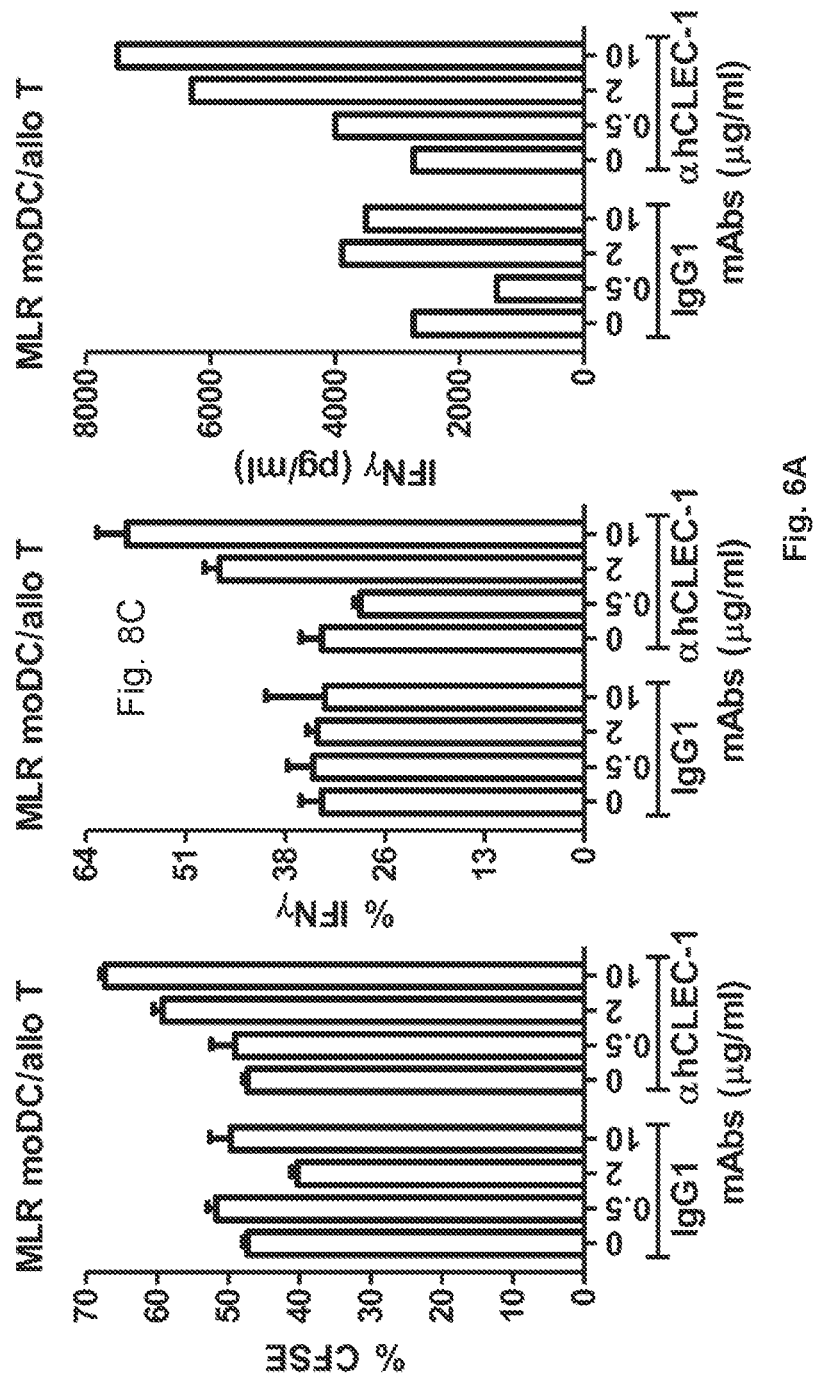

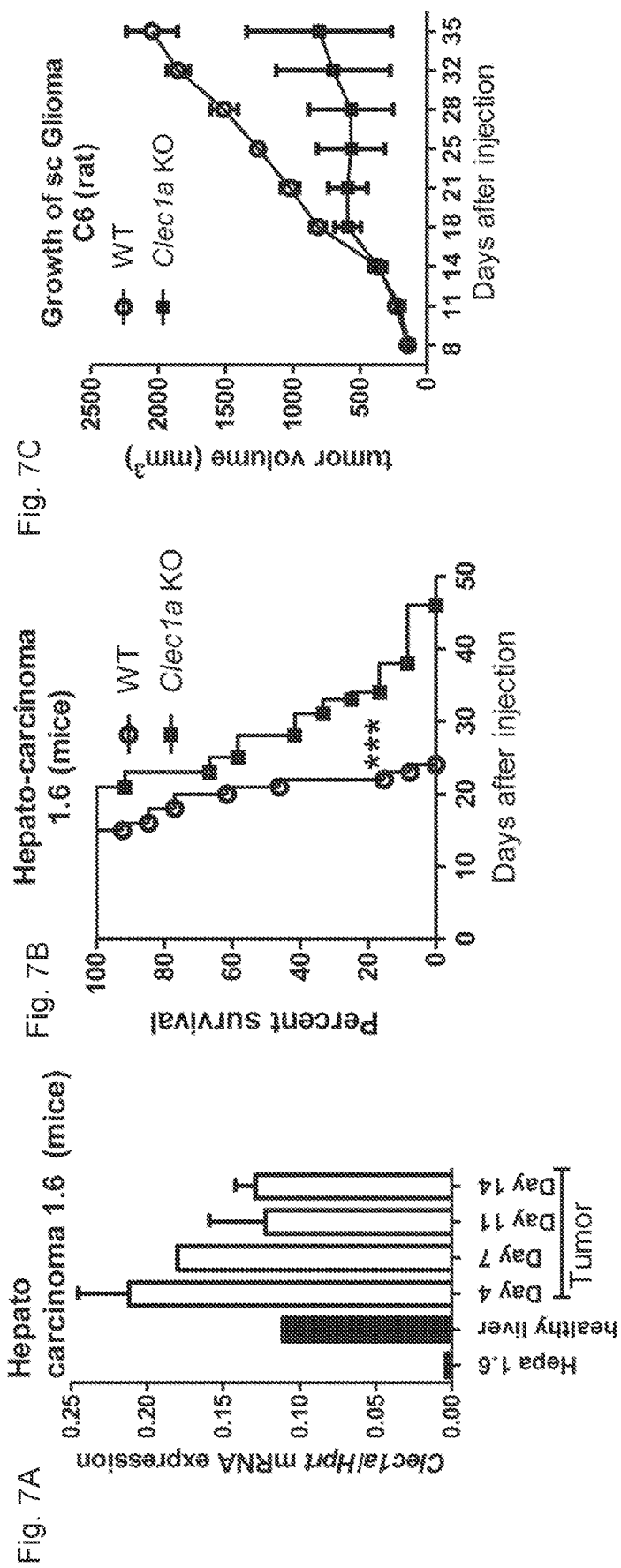

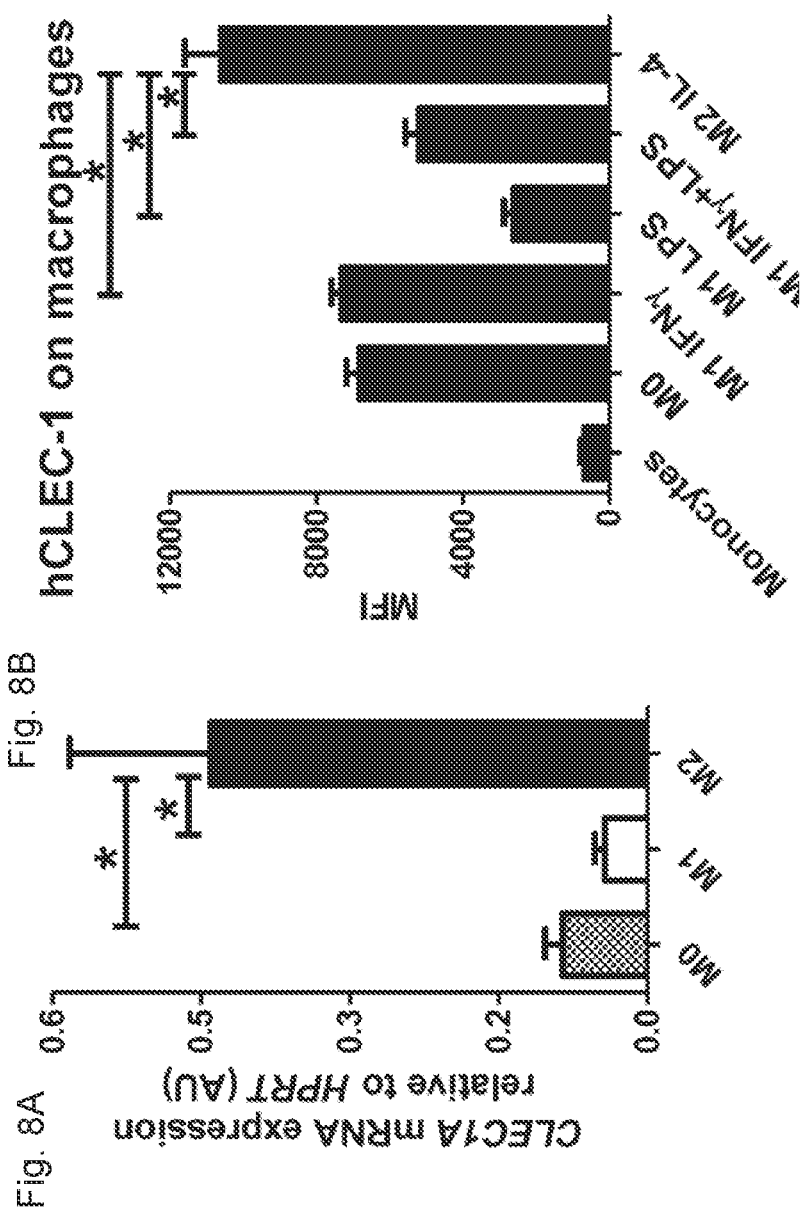

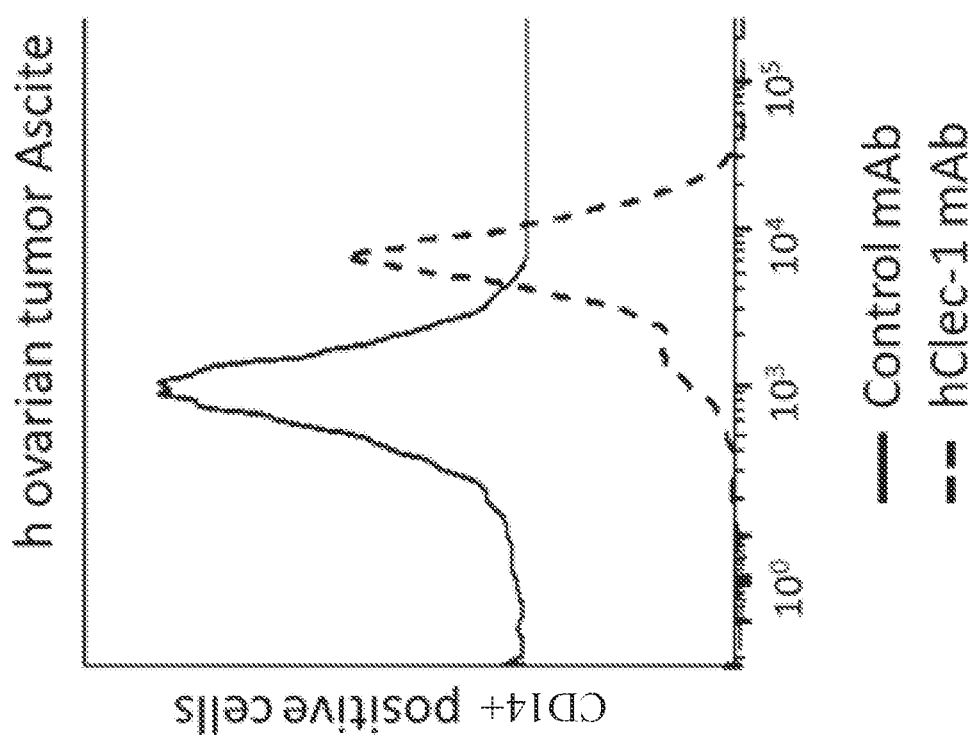

METHODS FOR PROMOTING T CELLS RESPONSE BY ADMINISTERING AN ANTAGONIST OF HUMAN C-TYPE LECTIN-LIKE RECEPTOR 1 (CLEC-1)

CROSS-REFERENCE TO RELATED APPLICATIONS

This application is the U.S. National Stage of International Application PCT/EP2017/076911, filed Oct. 20, 2017, which claims the benefit of European Application 17305988.2 filed Jul. 24, 2017, and European Application 16306381.1 filed Oct. 21, 2016.

FIELD OF THE INVENTION

The present invention relates to methods for promoting T cells response.

BACKGROUND OF THE INVENTION

Cancer is a major concern since it is a leading cause of death worldwide accounting for 8.2 million deaths in 2012 (world cancer report, 2014, World Health Organization). For example, cancer is the second most common cause of death in the US, exceeded only by heart diseases, and accounts for nearly 1 of every 4 deaths (cancer facts and figures 2015, American Cancer Society). Despite numerous existing treatments, it still a need for an improved method of treating cancer.

The T cells responses represent a key element of antitumor immune responses. The antitumor T-cell response remains poorly known, but several studies showed that cytotoxic CD8-type and helper CD4-type responses play a pivotal role (Motz, G T and Coukos, G (2013). Deciphering and reversing tumor immune suppression. Immunity 39: 61-73) (Bos, R and Sherman, L A (2010). CD4+ T-cell help in the tumor milieu is required for recruitment and cytolytic function of CD8+T lymphocytes. Cancer Res 70: 8368-8377) (Tosolini, M, et al. (2011). Clinical impact of different classes of infiltrating T cytotoxic and helper cells (Th1, Th2, Treg, Th17) in patients with colorectal cancer. Cancer Res 71: 1263-1271). Moreover, Th17 cells drive antitumor immune responses by recruiting immune cells into tumors, activating effector CD8+ T cells, or even directly by converting toward Th1 phenotype and producing IFN-γ (Th17 Cell Plasticity and Functions in Cancer Immunity, Leslie Guéry and Stéphanie Hugues, BioMed Research International, Volume 2015 (2015)).

Among the most promising approaches to activate therapeutic antitumor immunity is the blockade of immune checkpoints. Immune checkpoints refer to a plethora of inhibitory pathways hardwired into the immune system that are crucial for maintaining self-tolerance and minimize collateral tissue damage. It is now clear that tumors co-opt certain immune-checkpoint pathways notably via myeloid cells as a major mechanism of immune resistance (Couzin-Frankel 2013; De Henau, Rausch et al. 2016).

The past few years, accumulating evidence demonstrates that tumors use physiological processes of inhibitory C-type lectin receptors (CLRs) particularly those involved with wound healing to suppress myeloid cell activation and promote immune evasion. CLRs have the particularity to recognize abnormal glycosylation by tumor cells but also more diverse ligands such as lipids, proteins or DAMPs released by dying cells (Geijtenbeek and Gringhuis 2009; Yan, Kamiya et al. 2015). Several experimental studies demonstrate that CLRs contribute to cancer progression and metastatic spread by their function in cell-adhesion or in T-cell response shaping (Yan, Kamiya et al. 2015; Ding, Yao et al. 2017). For example, the immunomodulatory receptors DC-SIGN, MINCLE, DCIR and BDCA-2 have been shown to inhibit myeloid cell activation, inflammation and be critical to drive Foxp3$^+$ CD4$^+$ CD25$^+$ Tregs expansion (Yan, Kamiya et al. 2015; Ding, Yao et al. 2017). DC-SIGN recognize carcinoembryonic antigen overexpressed on almost all human carcinoma (Nonaka, Ma et al. 2008) and promotes the secretion of the immunosuppressive cytokines IL-10 and IL-6 by myeloid cells. Besides, polymorphisms in DC-SIGN gene promoter were found to be associated with increased risk in colorectal cancer patients (Lu, Bevier et al. 2013). MINCLE was shown to be enhanced in tumor infiltrating leukocytes in pancreatic ductal adenocarcinoma and especially by myeloid suppressive cells (MSCs). Ligation of MINCLE with SAP130 (a subunit of the histone deacetylase complex) released from dying cells induces strong peri-tumoral suppression (Seifert, Werba et al. 2016). Similarly, the CLR LOX-1 has been shown to be specifically enhanced at the cell surface of blood or tumor-infiltrating neutrophils (15 to 50%) in cancer patients whereas is nearly undetectable in blood of healthy donors (Condamine, Dominguez et al. 2016). In this study, they showed that endoplasmic reticulum stress induces LOX-1 expression and convert neutrophils to MSCs with strong suppressive function.

Conversely, triggering signaling of activating CLR such as DECTIN-1, has been shown to mount anti-tumor immunity and to decrease Tregs and MSCs (Tian, Ma et al. 2013). Administration of beta-glucans, a ligand of DECTIN-1 inhibits tumor growth in murine carcinoma models (Li, Cai et al. 2010; Masuda, Inoue et al. 2013; Tian, Ma et al. 2013), in human melanoma, neuroblastoma, lymphoma xenograft models (Modak, Koehne et al. 2005) as well as in human ovarian and gastric cancer (Inoue, Tanaka et al. 1993; Oba, Kobayashi et al. 2009).

Therefore, targeting inhibitory CLRs that are particularly induced in this microenvironment represents promising therapeutic strategy to enhance myeloid cells activation and anti-tumor immunity.

In the past, the inventors identified the C-type lectin-like receptor-1 (CLEC-1) to be up-regulated in a model of allograft tolerance in rodent (Thebault, Lhermite et al. 2009). CLEC-1 belongs to the DECTIN-1 cluster of the C-Type Lectin-like receptors (Plato, Willment et al. 2013) and although identified a long time ago, ligands and signaling remain uncharacterized. CLEC-1 belongs to the DECTIN-1 cluster of CTLRs including CLEC-2, DECTIN-1, CLEC-9A, MICL, MAH and LOX-1, and although identified a long time ago (Colonna M, Samaridis J, Angman L. Molecular characterization of two novel C-type lectin-like receptors, one of which is selectively expressed in human dendritic cells. Eur J Immunol. 2000; 30(2):697-704), the ligands, the downstream signaling and the biological effects remain uncharacterized. CLEC-1 does not contain an immunoreceptor tyrosine-based activation (ITAM) or inhibitory (ITIM) motif in the cytoplasmic tail but rather a tyrosine residue in a non-characterized signaling sequence (Flornes L M, Nylenna O, Saether P C, Daws M R, Dissen E, Fossum S. The complete inventory of receptors encoded by the rat natural killer cell gene complex. Immunogenetics. 2010; 62(8):521-530). However, it is unknown whether this motif is subject to phosphorylation or whether CLEC-1 requires as for other CTLRs an adaptor chain for stable expression and signaling. CLEC-1 contains also as Dectin-1, DC-SIGN or CLEC-2 a tri-acidic motif [DDD]. Interestingly, this tri-acidic motif has been shown for Dectin-1 to modulate Raf-1 activity and to repress the Caspase recruitment domain-containing protein 9 (Card9)-dependent NF-κB pathway induced by most of CTLRs to reprogram the set of secreted cytokines and the balance of subsequent Th1 and Th17 cell differentiation (Gringhuis S I, den Dunnen J, Litjens M, et al. Dectin-1 directs T helper cell differentiation by controlling noncanonical NF-kappaB activation through Raf-1 and Syk. Nat Immunol. 2009; 10(2):203-213). Very few has been described so far on human CLEC-1 protein expression, regulation and function. There is solely one publication about CLEC-1 expression which discloses that human CLEC-1 could only be detected intracellularly in endothelial cells with a staining pattern resembling endoplasmic reticulum proteins and that neither TGF-β nor inflammatory stimuli could promote significant translocation to the cell surface (The human C-type lectin-like receptor CLEC-1 is upregulated by TGF-β and primarily localized in the endoplasmic membrane compartment. Sattler et al., ScandJImmunol. 2012 March; 75(3):282-92). Thus, the only information available in the state of the art on hCLEC-1 (ie, intracellular localisation in endothelial cells) is contrary to what was known in the rat (i.e; rCLEC-1 localised on the surface of endothelial and myeloid cells).

The present inventors showed for the first time that CLEC-1 is expressed at the cell-surface by conventional DCs (cDCs) and by small subsets of monocytes and DCs in human blood and is enhanced by the immunosuppressive cytokine TGFβ. They demonstrated in both rodent and human that CLEC-1 acts as an inhibitory receptor in myeloid cells and prevent IL12p40 expression and downstream Th1 and Th17 in vivo responses.

They also showed that human T cells proliferation and human IFN-gamma are increased using anti-hCLEC-1 antibodies as antagonist of CLEC-1. They also demonstrated that mice deficient in CLEC-1 are better resistant to tumor growth and exhibit an increased survival rate in a hepatocarcinoma mice model. The inventors showed that human CLEC-1 is expressed by M2-type pro-tumoral macrophages, by myeloid cells from pleural effusion mesothelioma and from ovarian tumor ascites. Therefore, CLEC-1 as a cell-surface receptor may represent a useful therapeutic tool to enhance anti-tumor immunity in a clinical setting.

SUMMARY OF THE INVENTION

The present invention relates to methods for promoting T cells response. In particular, the invention is defined by the claims.

DETAILED DESCRIPTION OF THE INVENTION

Surprisingly, the inventors examined the expression and function of CLEC-1 in human DCs and demonstrated for the first time a cell-surface expression. The inventors also showed in human that h-CLEC-1 is expressed by M2-type pro-tumoral macrophages, by myeloid cells from pleural effusion mesothelioma and from ovarian tumor ascites. They investigated its functional role following triggering on orchestration of T-cell responses.

In addition, they investigated in vitro and in vivo with CLEC-1 deficient rats and rat CLEC-1 Fc fusion protein, the consequence of disruption of CLEC-1 signalling on DC function and downstream T-cell immunity. Disruption of CLEC-1 signalling enhances in vitro Th17 activation and in vivo enhances T cell priming and Th17 and Th1 activation. Their results clearly indicate that CLEC-1 in DCs inhibits the degree and quality of downstream Th17 and Th1 cell activation and as a cell-surface receptor may provide a therapeutic tool to manipulate T cell response. The inventors also showed that human T cells proliferation and human IFN-gamma are increased using anti-hCLEC-1 antibodies as antagonist of CLEC-1. They also demonstrated that mice deficient in CLEC-1 are better resistant to tumor growth and exhibit an increased survival rate in a hepatocarcinoma mice model. Results show that CLEC-1 play the role of inhibitory receptor in myeloid cells by raising activation threshold. CLEC-1 inactivation increases T cells proliferation and both Th1 and Th17 polarization.

Accordingly, a first aspect of the present invention relates to a method of promoting T cells response in a subject in need thereof comprising administering to the subject a therapeutically effective amount of an antagonist of CLEC-1.

The method according to the invention wherein the subject suffers from cancer.

Another aspect of the present invention relates to a composition, in particular a pharmaceutical composition, comprising the CLEC-1 antagonist of the invention.

As used herein, the term "T cells" has its general meaning in the art and refers to T lymphocyte which is a type of lymphocyte having a T-cell receptor on the cell surface and playing a central role in cell-mediated immunity.

As used herein, the term "T cells response" refers to any biological process involving T cells proliferation and/or cytokine synthesis.

The T cells response can be determined by various methods well known from one skilled in the art by assessing T cells proliferation and/or cytokine synthesis. In one embodiment, T cells response is determined by performing a mixed leukocyte reaction (MLR) consisted of purified T cells isolated from peripheral blood mixed with allogenic monocytes derived dendritic cells expressing CLEC-1. Proliferation of T cells can be assessed by carboxyfluorescein succinimidyl ester dilution and IFNγ expression can be assessed by flow cytometry in T cells and by ELISA in supernatants.

As used herein, the term "subject" denotes a mammal, such as a rodent, a feline, a canine, and a primate. Preferably, a subject according to the invention is a human.

The terms "cancer" has its general meaning in the art and refers to a group of diseases involving abnormal cell growth with the potential to invade or spread to other parts of the body. The term "cancer" further encompasses both primary and metastatic cancers. Examples of cancers that may treated by methods and compositions of the invention include, but are not limited to, cancer cells from the bladder, blood, bone, bone marrow, brain, breast, colon, esophagus, gastrointestinal, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; non encapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malign melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brennertumor, malignant; phyllodestumor, malignant; synovial sarcoma; mesothelioma, malignant; dysgerminoma; embryonal carcinoma; teratoma, malignant; strumaovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblasticodontosarcoma; ameloblastoma, malignant; ameloblasticfibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocyticleukemia; mast cell leukemia; megakaryoblasticleukemia; myeloid sarcoma; and hairy cell leukemia.

In some embodiments, the subject suffers from a cancer selected from the group consisting of bile duct cancer, bladder cancer, bone cancer, brain and central nervous system cancer, breast cancer, Castleman disease cervical cancer, colorectal cancer, endometrial cancer, esophagus cancer, gallbladder cancer, gastrointestinal carcinoid tumors, Hodgkin's disease, non-Hodgkin's lymphoma, Kaposi's sarcoma, kidney cancer, laryngeal and hypopharyngeal cancer, liver cancer, lung cancer, mesothelioma, plasmacytoma, nasal cavity and paranasal sinus cancer, nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma, salivary gland cancer, skin cancer, stomach cancer, testicular cancer, thymus cancer, thyroid cancer, vaginal cancer, vulvar cancer, and uterine cancer.

In one embodiment, cancer is liver cancer.
In one embodiment, cancer is hepatocarcinoma.
In one embodiment, cancer is ovarian cancer.
In one embodiment, cancer is glioma.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. The term "treatment" encompasses the prophylactic treatment. As used herein, the term "prevent" refers to the reduction in the risk of acquiring or developing a given condition.

As used herein, the term "CLEC-1" has its general meaning in the art and refers to C-type lectin-like receptor-1, particularly from a mammal species, more particularly a human CLEC-1.CLEC-1 belongs to the DECTIN-1 cluster of C type-lectin like receptors (CTLRs) including CLEC-2, DECTIN-1, CLEC-9A, MICL, MAH and LOX-1.

Preferably, the term "human CLEC-1" refers to the protein of amino acid sequence referenced by the Q8NC01 Uniprot accession number and encoded by CLEC1A gene referenced by the 51267 NCBI accession number.

In particular, the CLEC-1 antagonist is an antagonist of human CLEC-1.

As used herein, the term "CLEC-1 antagonist" has its general meaning in the art and refers to any compound, natural or synthetic, that blocks, suppresses, or reduces the biological activity of CLEC-1. In particular, the CLEC-1 antagonist inhibits the interactions between the receptor CLEC-1 and at least one of its ligands, more particularly and all of its ligands. More particularly, the CLEC-1 antagonist can bind to receptor CLEC-1 or to any one of its ligands. The CLEC-1 antagonist enhances T cells response, in particular increases T cells proliferation and/or cytokine synthesis such as IFNgamma.

For example, CLEC-1 antagonist can be identify by the following method comprising the steps consisting of:
  a) providing a plurality of cells expressing CLEC-1 on their surface;
  b) incubating said cells with a candidate compound;
  c) determining whether said candidate compound binds to and blocks, suppresses, or reduces the biological activity of CLEC-1, and in particular whether said candidate promotes T cell response;

and d) selecting the candidate compound that binds to and blocks, suppresses, or reduces the biological activity of CLEC-1 and in particular promotes T cell response.

In some embodiments, the CLEC-1 antagonist is a small organic molecule. The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more in particular up to 2000 Da, and most in particular up to about 1000 Da.

In some embodiments, the CLEC-1 antagonist is an antibody or an antigen-binding fragment thereof. In some embodiments, the CLEC-1 antagonist is an antibody or an antigen-binding fragment thereof which specifically binds to CLEC-1.

As used herein, the term "specifically binds to" or "binds specifically" refers to the ability of an antigen receptor to bind to an antigen with an affinity of at least about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or more, and/or bind to a target with an affinity that is at least two-fold greater than its affinity for a nonspecific antigen.

The affinity can be determined by various methods well known from one skilled in the art. These methods include, but are not limited to, Biacore Analysis, Blitz analysis and Scatchard plot.

In an embodiment, the antibody or antigen-binding fragment thereof according to the invention has a KD value inferior or equal to $10^{-8}$ M, preferably inferior or equal to $10^{-9}$ M for CLEC-1, in particular for human CLEC-1, more preferably inferior or equal to $1 \cdot 10^{-10}$ M, as may be determined by biosensor analysis, particularly by Biacore Analysis.

In some embodiments, the antagonist of CLEC-1, in particular the antibody or antigen-binding fragment thereof according to the invention specifically binds to the extracellular domain of CLEC-1, particularly of human CLEC-1.

In one embodiment, the amino acid sequence of the extracellular domain of humanCLEC-1 is (SEQ ID NO: 1)
YYQLSNTGQDTISQMEERLGNTSQELQSLQVQNIKLAGSLQHVAEKLCRE

LYNKAGAHRCSPCTEQWKWHGDNCYQFYKDSKSWEDCKYFCLSENSTMLK

INKQEDLEFAASQSYSEFFYSYWTGLLRPDSGKAWLWMDGTPFTSELFHI

IIDVTSPRSRDCVAILNGMIFSKDCKELKRCVCERRAGMVKPESLHVPPE

TLGEGD.

In one embodiment, the amino acid sequence which is recognized by the antagonist of CLEC-1, in particular by the antibody or antigen-binding fragment thereof of the invention is (SEQ ID NO: 2)
CERRAGMVKPESLHVPPETLGEGD.

As used herein, "antibody" includes both naturally occurring and non-naturally occurring antibodies. Specifically, "antibody" includes polyclonal, monoclonal, recombinant (including chimeric and humanized), bispecific, multispecific and modified antibodies, as well as monovalent and divalent antigen-binding fragments thereof. Furthermore, "antibody" includes chimeric antibodies, wholly synthetic antibodies, single chain antibodies, and fragments thereof.

The antibody may be a human or nonhuman antibody. A nonhuman antibody may be humanized by recombinant methods to reduce its immunogenicity in man.

As used herein, a "modified antibody" corresponds to a molecule comprising an antibody or an antigen-binding fragment thereof, wherein said antibody or fragment thereof is associated with a functionally different molecule.

In one embodiment of the antibodies or portions thereof described herein, the antibody is a monoclonal antibody. In one embodiment of the antibodies or portions thereof described herein, the antibody is a full human monoclonal antibody. In one embodiment of the antibodies or portions thereof described herein, the antibody is a polyclonal antibody. In one embodiment of the antibodies or portions thereof described herein, the antibody is a humanized antibody. In one embodiment of the antibodies or portions thereof described herein, the antibody is a chimeric antibody. In one embodiment of the antibodies or portions thereof described herein, the portion of the antibody comprises a light chain of the antibody. In one embodiment of the antibodies or portions thereof described herein, the portion of the antibody comprises a heavy chain of the antibody. In one embodiment of the antibodies or portions thereof described herein, the portion of the antibody comprises a Fab portion of the antibody. In one embodiment of the antibodies or portions thereof described herein, the portion of the antibody comprises a F(ab')2 portion of the antibody. In one embodiment of the antibodies or portions thereof described herein, the portion of the antibody comprises a Fc portion of the antibody. In one embodiment of the antibodies or portions thereof described herein, the portion of the antibody comprises aFv portion of the antibody. In one embodiment of the antibodies or portions thereof described herein, the portion of the antibody comprises a variable domain of the antibody. In one embodiment of the antibodies or portions thereof described herein, the portion of the antibody comprises one or more CDR domains of the antibody.

Antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with antigenic forms of CLEC-1. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes. Briefly, the recombinant CLEC-1 may be provided by expression with recombinant cell lines. In particular, CLEC-1 may be provided in the form of human cells expressing CLEC-1 at their surface. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

In one embodiment, the antagonist of CLEC-1 is selected from the group consisting of chimeric antibodies, humanized antibodies and fully human monoclonal antibodies.

In one embodiment, the antibody of the invention is a chimeric antibody, particularly a chimeric mouse/human antibody. According to the invention, the term "chimeric antibody" refers to an antibody which comprises a VH domain and a VL domain of a non-human antibody, and a CH domain and a CL domain of a human antibody.

In some embodiments, the antibody is a humanized antibody, in particular a humanized monoclonal antibody. As used herein, "humanized" describes antibodies issued from non-human species whose protein sequences have been modified to increase their identity to antibody variants produced naturally in human. Accordingly having been originally obtained in animals, especially in rodents and in particular in rats, following immunization of animals and production of antibodies, particularly monoclonal antibodies from hybridoma, the antibodies are then modified in their VH and/or VL sequences by substitution of amino acid residues, in the framework and optionally in addition in the CDR sequences to obtain humanized antibodies. Particularly, said humanized antibody has less than 10% of mutated amino acid residues, preferably one or no mutated amino acid residue, in individually considered CDR regions with respect to the original CDRs regions. Methods of humanization include, but are not limited to, those described in U.S. Pat. Nos. 4,816,567, 5,225,539, 5,585,089, 5,693,761, 5,693,762 and 5,859,205, which are hereby incorporated by reference.

In some embodiments, the antibody is a fully human antibody, in particular a fully human monoclonal antibody. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans. In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

In another embodiment, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®".

In some embodiments, the antibody of the present invention does not mediate antibody-dependent cell-mediated cytotoxicity and thus does not comprise an Fc portion that induces antibody dependent cellular cytotoxicity (ADCC). In some embodiments, the antibody of the present invention does not lead, directly or indirectly, to the depletion of cells expressing CLEC-1 (e.g. do not lead to a 10%, 20%, 50%, 60% or greater elimination or decrease in number of cells expressing CLEC-1). In some embodiments, the antibody of the present invention lacks an Fc domain (e.g. lacks a CH2 and/or CH3 domain) or comprises an Fc domain of IgG2 or IgG4 isotype.

As used herein the term "antibody-dependent cell-mediated cytotoxicity" or 'ADCC' refer to a cell-mediated reaction in which non-specific cytotoxic cells (e.g., Natural Killer (NK) cells, neutrophils, and macrophages) recognize bound antibody on a target cell and subsequently cause lysis of the target cell. While not wishing to be limited to any particular mechanism of action, these cytotoxic cells that mediate ADCC generally express Fc receptors (FcRs).

As used herein, the term "depleting", with respect to cells expressing CLEC-1, means a process, method, or compound that can kill, eliminate, lyse or induce such killing, elimination or lysis, so as to negatively affect the number of cells expressing CLEC-1 present in a sample or in a subject.

In one embodiment, the CLEC-1 antagonist is an antigen-binding antibody mimetic.

As used herein the term "antigen-binding antibody mimetic" refers to artificial proteins, peptides and any chemical compounds with the capacity to bind antigens mimicking that of antibodies.

Such mimetics comprise affitins and anticalins as well as aptamers (peptide aptamers and oligonucleotide aptamers).

In one embodiment, the CLEC-1 antagonist is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence. Peptide aptamers consists of a conformationally constrained antibody variable region displayed by a platform protein, such as $E.\ coli$ Thioredoxin A that are selected from combinatorial libraries by two hybrid methods.

In some embodiments, the CLEC-1 antagonist is a polypeptide.

The term "polypeptide" means herein a polymer of amino acids having no specific length. Thus, peptides, oligopeptides and proteins are included in the definition of "polypeptide" and these terms are used interchangeably throughout the specification, as well as in the claims. The term "polypeptide" does not exclude post-translational modifications that include but are not limited to phosphorylation, acetylation, glycosylation and the like.

In one embodiment, the polypeptide of the invention has a length comprised between 2 and 200 amino acids. In one embodiment, the polypeptide of the invention has a length comprised between 2 and 190, in particular between 10 and 180, between 10 and 170, between 10 and 160, between 10 and 150, between 10 and 140, between 10 and 130, between 10 and 120, between 10 and 110 amino acids. In one embodiment, the polypeptide of the invention has a length comprised between 10 and 100 amino acids. In one embodiment, the polypeptide of the invention has a length comprised between 50 and 100 amino acids. In one embodiment, the polypeptide of the invention has a length of 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 amino acids.

In a particular embodiment, the polypeptide is a functional equivalent of CLEC-1. As used herein, a "functional equivalent" of CLEC-1 is a compound which is capable of binding to at least one CLEC-1 ligand, thereby preventing its interaction with CLEC-1. The term "functional equivalent" includes fragments, mutants, and muteins of CLEC-1. The term "functionally equivalent" thus includes any equivalent of CLEC-1 obtained by altering the amino acid sequence, for example by one or more amino acid deletions, substitutions or additions such that the protein analogue retains the ability to bind to its ligand. Amino acid substitutions may be made, for example, by point mutation of the DNA encoding the amino acid sequence.

Functional equivalents include but are not limited to molecules that bind to a ligand of CLEC-1 and comprise all or a portion of the extracellular domains of CLEC-1 so as to form a soluble receptor that is capable to trap the ligand of CLEC-1. Thus, the functional equivalents include soluble forms of CLEC-1. A suitable soluble form of these proteins, or functional equivalents thereof, might comprise, for example, a truncated form of the protein from which the transmembrane domain has been removed by chemical, proteolytic or recombinant methods. Particularly, the functional equivalent consisting of a sequence having at least 80% identity, more particularly at least 85%, at least 86%, at least 87%, at least 88%, at least 89%, at least 90%, at least 91%, at least 92%, at least 93%, at least 94%, at least 95%, at least 96%, at least 97%, at least 98% and even more particularly at least 99% of identity with the corresponding protein over the entire length of the corresponding protein. As used herein, the term "corresponding protein" refers to the protein for which the functional equivalent of the invention has similar function. The percentages of identity to which reference is made in the presentation of the present invention are determined on the basis of a global alignment of sequences to be compared, that is to say, on an alignment of sequences over their entire length, using for example the algorithm of Needleman and Wunsch 1970. This sequence comparison can be done for example using the needle software by using the parameter "Gap open" equal to 10.0, the parameter "Gap Extend" equal to 0.5, and a matrix "BLOSUM 62". Software such as needle is available on the website ebi.ac.uk worldwide, under the name "needle". The term "a functionally equivalent fragment" as used herein also may mean any fragment or assembly of fragments of CLEC-1 that binds to a ligand of CLEC-1. Accordingly, the present invention provides a polypeptide, in particular a functional equivalent, capable of inhibiting binding of CLEC-1 to at least one ligand of CLEC-1, which polypeptide comprises consecutive amino acids having a sequence which corresponds to the sequence of at least a portion of an extracellular domain of CLEC-1, which portion binds to a ligand of CLEC-1. In some embodiments, the polypeptide, in particular the functional equivalent, corresponds to an extracellular domain of CLEC-1.

In some embodiments, the functional equivalent of CLEC-1 is fused to a heterologous polypeptide to form a fusion protein. As used herein, a "fusion protein" comprises all or part (typically biologically active) of a functional equivalent of the present invention operably linked to a heterologous polypeptide (i.e., a polypeptide other than the same polypeptide). Within the fusion protein, the term "operably linked" is intended to indicate that the functional equivalent of the present invention and the heterologous polypeptide are fused in-frame to each other. The heterologous polypeptide can be fused to the N-terminus or C-terminus of the functional equivalent of the present invention.

In some embodiments, the functional equivalent of CLEC-1 is fused to an immunoglobulin constant domain (Fc region) to form an immunoadhesin. Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use. In some embodiments, the Fc region is a native sequence Fc region. In some embodiments, the Fc region is a variant Fc region. In still another embodiment, the Fc region is a functional Fc region. As used herein, the term "Fc region" is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The adhesion portion and the immunoglobulin sequence portion of the immunoadhesin may be linked by a minimal linker. The immunoglobulin sequence typically, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but typically IgG1 or IgG4. In some embodiments, the functional equivalent of CLEC-1 and the immunoglobulin sequence portion of the immunoadhesin are linked by a minimal linker. As used herein, the term "linker" refers to a sequence of at least one amino acid that links the polypeptide of the invention and the immunoglobulin sequence portion. Such a linker may be useful to prevent steric hindrances. In some embodiments, the linker has 4; 5; 6; 7; 8; 9; 10; 11; 12; 13; 14; 15; 16; 17; 18; 19; 20; 21; 22; 23; 24; 25; 26; 27; 28; 29; 30 amino acid residues. However, the upper limit is not critical but is chosen for reasons of convenience regarding e.g. biopharmaceutical production of such polypeptides. The linker sequence may be a naturally occurring sequence or a non-naturally occurring sequence. If used for therapeutical purposes, the linker is typically non-immunogenic in the subject to which the immunoadhesin is administered. One useful group of linker sequences are linkers derived from the hinge region of heavy chain antibodies as described in WO 96/34103 and WO 94/04678. Other examples are poly-alanine linker sequences.

The polypeptides of the invention may be produced by any suitable means, as will be apparent to those of skill in the art. In order to produce sufficient amounts of polypeptides for use in accordance with the present invention, expression may conveniently be achieved by culturing under appropriate conditions recombinant host cells containing the polypeptide of the invention. In particular, the polypeptide is produced by recombinant means, by expression from an encoding nucleic acid molecule. Systems for cloning and expression of a polypeptide in a variety of different host cells are well known. When expressed in recombinant form, the polypeptide is in particular generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also preferred hosts for the production of recombinant protein, due to the ease with which bacteria may be manipulated and grown. A common, preferred bacterial host is E. coli.

The polypeptides of the invention, fragments thereof and fusion proteins according to the invention can exhibit post-translational modifications, including, but not limited to glycosylations, (e.g., N-linked or O-linked glycosylations), myristylations, palmitylations, acetylations and phosphorylations (e.g., serine/threonine or tyrosine).

In some embodiments, it is contemplated that polypeptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

A further aspect of the present invention relates to a method of treating cancer, particularly by promoting T cells response, in a subject in need thereof comprising administering to the subject a therapeutically effective amount of an antagonist of CLEC-1.

The present invention thus relates to an antagonist of CLEC-1 for use in the treatment of cancer, particularly by promoting T cells response.

The present invention thus relates to the use of an antagonist of CLEC-1 for the manufacture of a medicament for the treatment of cancer, particularly by promoting T cells response.

In some embodiments, the CLEC-1 antagonist of the invention is administered to the subject with a therapeutically effective amount.

The terms "administer" or "administration" refer to the act of injecting or otherwise physically delivering a substance as it exists outside the body (e.g., CLEC-1 antagonist of the present invention) into the subject, such as by mucosal, intradermal, intravenous, subcutaneous, intramuscular, intra-articular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

By a "therapeutically effective amount" is meant a sufficient amount of CLEC-1 antagonist for use in a method for the treatment of cancer at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the severity of the cancer, the age, body weight, general health, sex and diet of the subject; the time of administration, route of administration, and rate of excretion of the specific compound employed; the duration of the treatment; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The compositions according to the invention are formulated for parenteral, transdermal, oral, rectal, subcutaneous, sublingual, topical or intranasal administration.

Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

In one embodiment, the compositions, in particular pharmaceutical compositions, according to the invention are formulated for parenteral administration. The pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

In a preferred embodiment, the compositions according to the invention are formulated for intravenous administration. In another embodiment, the compositions according to the invention are formulated for oral administration.

Typically, the active ingredient of the present invention (i.e. the CLEC-1 antagonist) is combined with pharmaceutically acceptable excipients, and optionally sustained-release matrices, such as biodegradable polymers, to form pharmaceutical compositions.

The term "pharmaceutically" or "pharmaceutically acceptable" refers to molecular entities and compositions that do not produce an adverse, allergic or other untoward reaction when administered to a mammal, especially a human, as appropriate.

A pharmaceutically acceptable carrier or excipient refers to a non-toxic solid, semi-solid or liquid filler, diluent, encapsulating material or formulation auxiliary of any type. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

In some embodiments, the CLEC-1 antagonist of the present invention is administered to the subject in combination with a second active ingredient.

Said second active ingredient include but is not limited to probiotics and therapeutic agents as described below.

The present invention relates thus to the combination of an antagonist of CLEC-1 with a second active ingredient for use in the treatment of cancer.

In some embodiments, the CLEC-1 antagonist of the present invention is administered to the subject in combination with a standard (conventional) treatment. The present invention relates thus to the combination of an antagonist of CLEC-1 with a conventional treatment for use in the treatment of cancer.

As used herein, the term "standard or conventional treatment" refers to any treatment of cancer (drug, radiotherapy, etc.) usually administrated to a subject who suffers from cancer.

In some embodiments, the CLEC-1 antagonist of the present invention is administered to the subject in combination with at least one further therapeutic agent, e.g. for treating cancers. Such administration may be simultaneous, separate or sequential. For simultaneous administration, the agents may be administered as one composition or as separate compositions, as appropriate. The further therapeutic agent is typically relevant for the disorder to be treated. Exemplary therapeutic agents include other anti-cancer antibodies, cytotoxic agents, chemotherapeutic agents, anti-angiogenic agents, anti-cancer immunogens, cell cycle control/apoptosis regulating agents, hormonal regulating agents, and other agents described below.

In some embodiments, the CLEC-1 antagonist of the present invention is used in combination with a chemotherapeutic agent, a targeted cancer therapy, an immunotherapeutic agent or radiotherapy.

In some embodiments, the CLEC-1 antagonist of the present invention is used in combination with a chemotherapeutic agent. The present invention relates thus to the combination of an antagonist of CLEC-1 with a chemotherapeutic agent for use in the treatment of cancer.

The term "chemotherapeutic agent" refers to chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a carnptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoproteinenediyneantiobioticchromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylamine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the CLEC-1 antagonist of the present invention is used in combination with a targeted cancer therapy. The present invention relates thus to the combination of an antagonist of CLEC-1 with a targeted therapy for use in the treatment of cancer.

Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names. In some embodiments, the targeted therapy consists of administering the subject with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S. Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signaling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), MK-2206 (8-[4-aminocyclobutyl)phenyl]-9-phenyl-1,2,4-triazolo[3,4-f][1,6]naphthyridin-3(2H)-one hydrochloride) derivatives thereof, analogs thereof, and combinations thereof. Additional tyrosine kinase inhibitors and related compounds suitable for use in the present invention are described in, for example, U.S. Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In some embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the CLEC-1 antagonist of the present invention is used in combination with an immunotherapeutic agent. The present invention relates thus to the combination of an antagonist of CLEC-1 with an immunotherapeutic agent for use in the treatment of cancer.

The term "immunotherapeutic agent," as used herein, refers to a compound, composition or treatment that indirectly or directly enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively, the immunotherapeutic treatment may consist of administering the subject with an amount of immune cells (T cells, NK, cells, dendritic cells, B cells . . . ). Immunotherapeutic agents can be non-specific, i.e. boost the immune system generally so that the human body becomes more effective in fighting the growth and/or spread of cancer cells, or they can be specific, i.e. targeted to the cancer cells themselves immunotherapy regimens may combine the use of non-specific and specific immunotherapeutic agents. Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants. A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors. Interferons (IFNs) contemplated by the present invention include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation). Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention. Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin). Combination compositions and combination administration methods of the present invention may also involve "whole cell" and "adoptive" immunotherapy methods. For instance, such methods may comprise infusion or re-infusion of immune system cells (for instance tumor-infiltrating lymphocytes (TILs), such as CC2+ and/or CD8+ T cells (for instance T cells expanded with tumor-specific antigens and/or genetic enhancements), antibody-expressing B cells or other antibody-producing or -presenting cells, dendritic cells (e.g., dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include Canvaxin™, APC-8015 (Dendreon), HSPPC-96 (Antigenics), and Melacine® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions.

In some embodiments, the CLEC-1 antagonist of the present invention is used in combination with radiotherapy. The present invention relates thus to the combination of an antagonist of CLEC-1 with radiotherapy for use in the treatment of cancer.

Radiotherapy may comprise radiation or associated administration of radiopharmaceuticals to a patient. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In one embodiment, the present invention relates to a method for screening a CLEC-1 antagonist comprising the steps consisting of:

a) providing a plurality of cells expressing CLEC-1 on their surface;

b) incubating said cells with a candidate compound;

c) determining whether said candidate compound binds to and blocks, suppresses, or reduces the biological activity of CLEC-1 and whether said candidate promotes T cell response;

and d) selecting the candidate compound that binds to and blocks, suppresses, or reduces the biological activity of CLEC-1 and promotes T cell response.

In a particular embodiment, the screening method of the invention may further comprise a step consisting of administering the candidate compound selected at step d) to an animal model to validate the protective and/or therapeutic effects of said candidate.

In general, such screening methods involve providing appropriate cells which express CLEC-1 on their surface. In particular, a nucleic acid encoding CLEC-1 may be employed to transfect cells to thereby express the receptor of the invention. Such a transfection may be accomplished by methods well known in the art.

The invention also relates to a method of preparation of a compound used for treating cancer, said method comprising a step of identifying CLEC-1 antagonist able to promoting T cells response.

The invention will be further illustrated by the following figures and examples. However, these examples and figures should not be interpreted in any way as limiting the scope of the present invention.

FIGURES

Figure 1B:
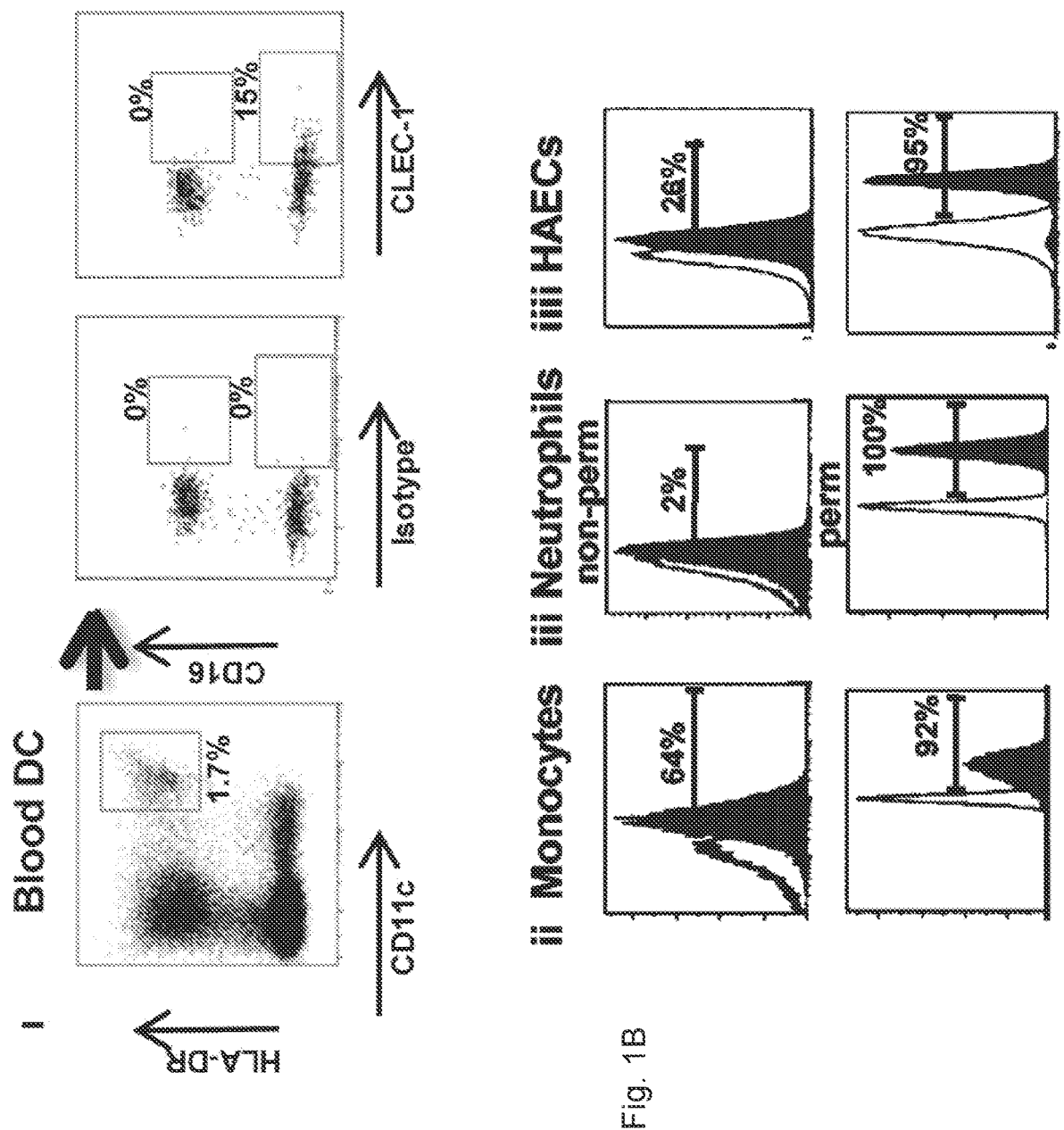
Figure 1C:
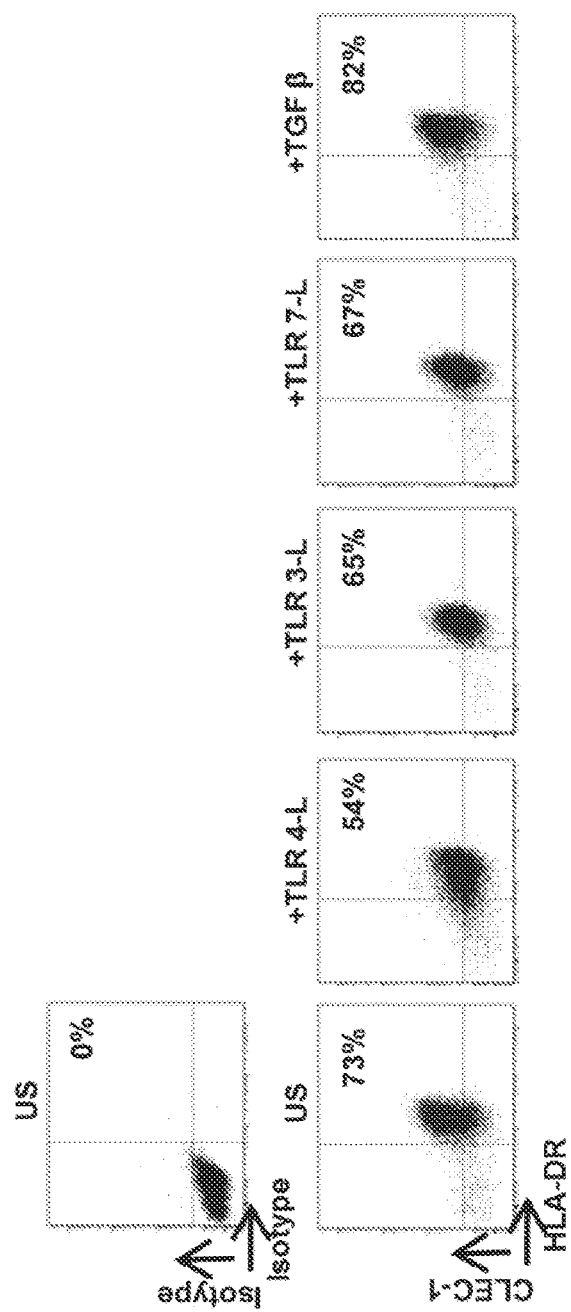
Figure 1C:
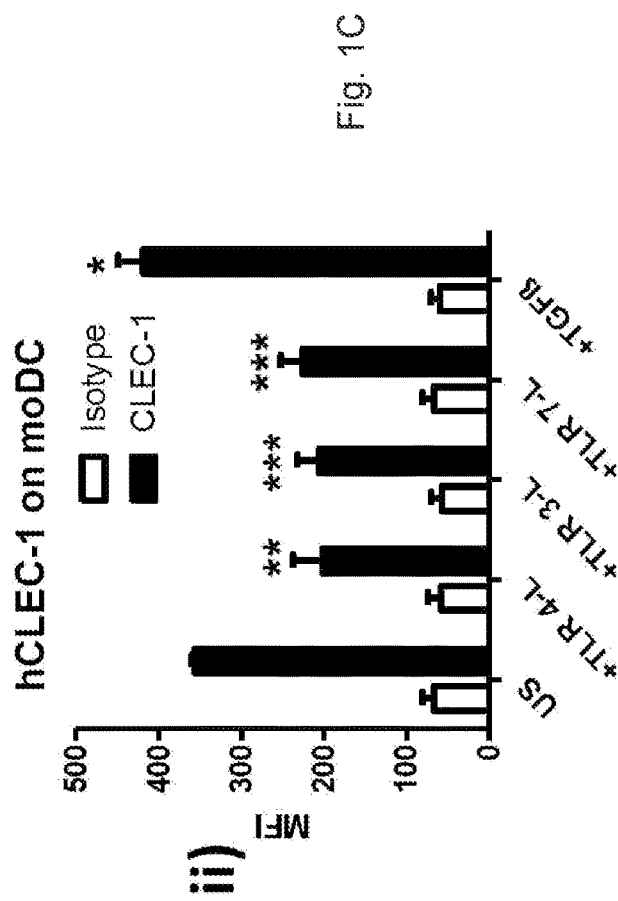

FIG. 1A-C: Expression and regulation of CLEC-1 mRNA and protein in human organs and cells.

FIG. 1A) CLEC-1 mRNA expression was assessed by quantitative RT-PCR in peripheral blood leucocytes (PBL), neutrophils (neutro), monocytes (mono), monocytes derived dendritic cells (moDC), Human aortic endothelial cells (HAECs), T and B cells.

FIG. 1B) Representative dot and histograms plots of IgG1 isotype or CLEC-1 staining evaluated by flow cytometry on human blood i) CD45+CD14-CD11c+ HLA-DR$^{high}$ DCs, ii) CD45+CD14+ monocytes iii) SSC$^{high}$ CD16+ neutrophils and on and in iiii) HAECs (extracellular and intracellular), with mAb anti-hCLEC-1. Histogram plot with the overlay image of CLEC-1 matching the histogram plot of cells stained with control isotype IgG1.

FIG. 1C) CLEC-1 expression on human moDCs. i) Representative dot plots of % of moDCs expressing cell-surface CLEC-1 (APC) and HLA-DR (FITC) evaluated by flow cytometry in unstimulated (US) cells and cells stimulated with LPS (TLR4-L), Poly I:C (TLR3-L), R848 (TLR7-L) and TGF-β as described in Material and Methods with mAb anti-hCLEC-1. IgG1 isotype was performed as control. ii) Histogram represents Mean fluorescence intensity (MFI) ±SEM of CLEC-1 staining in 6 independent experiments. Statistical analysis of CLEC-1 MFI staining was performed between US and stimulated cells.

Figure 2A:
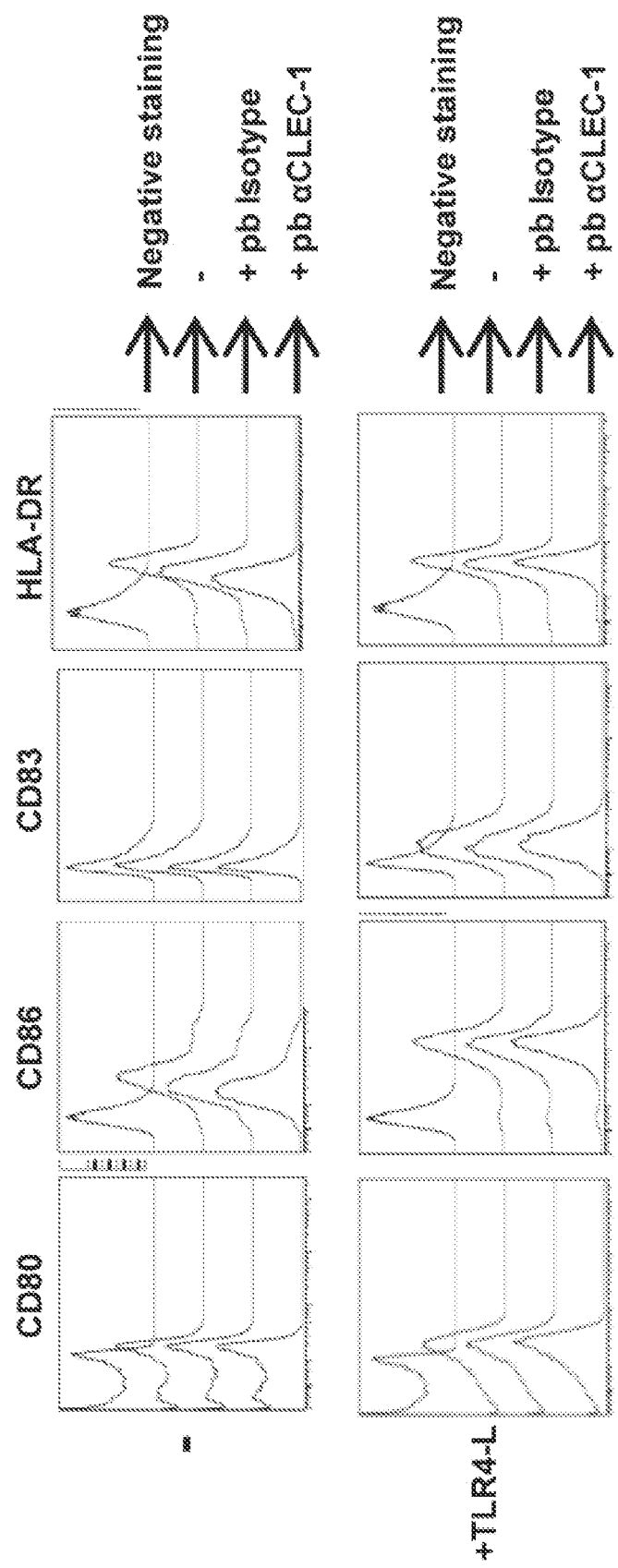
Figure 2B:
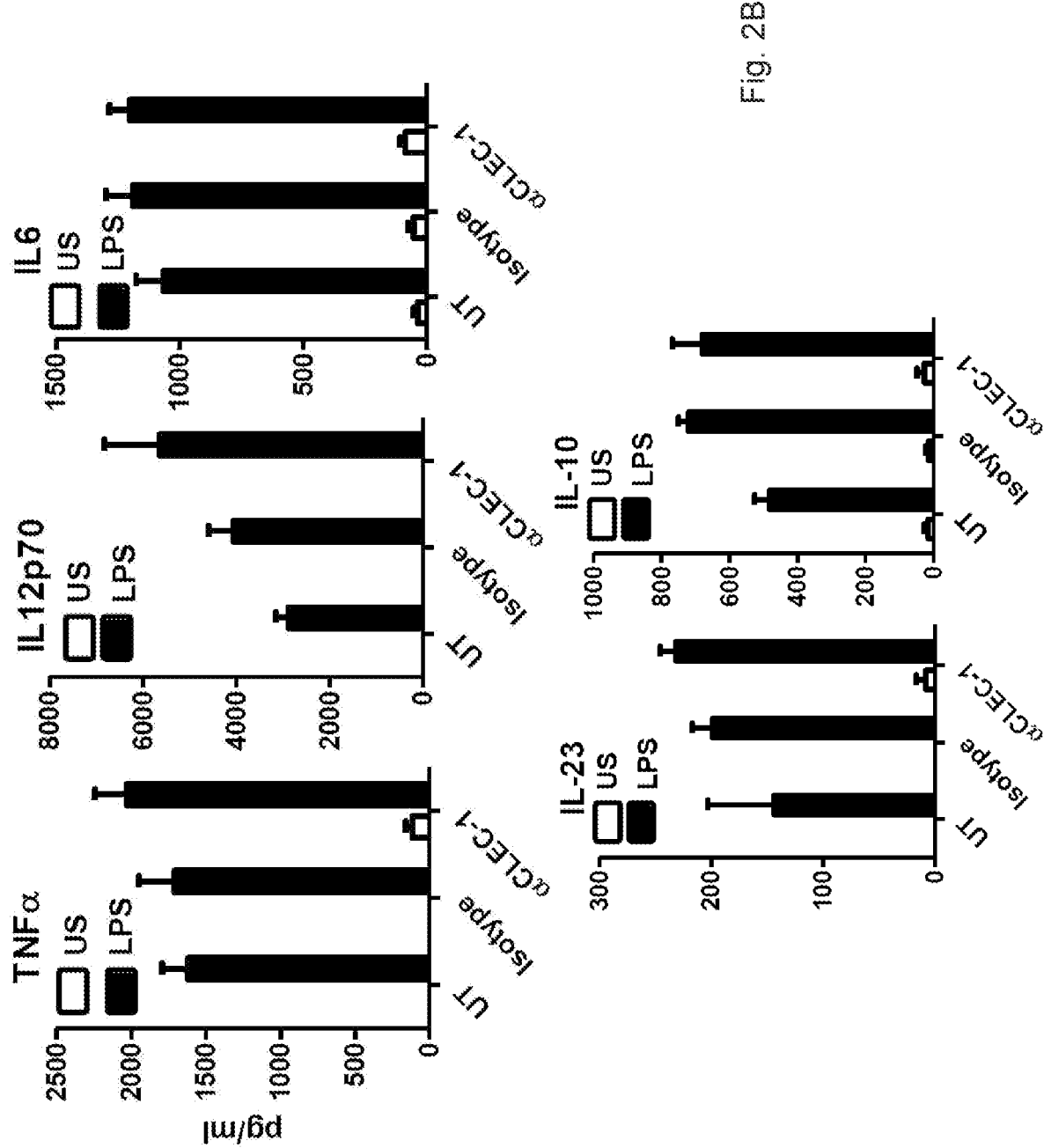
Figure 2C:
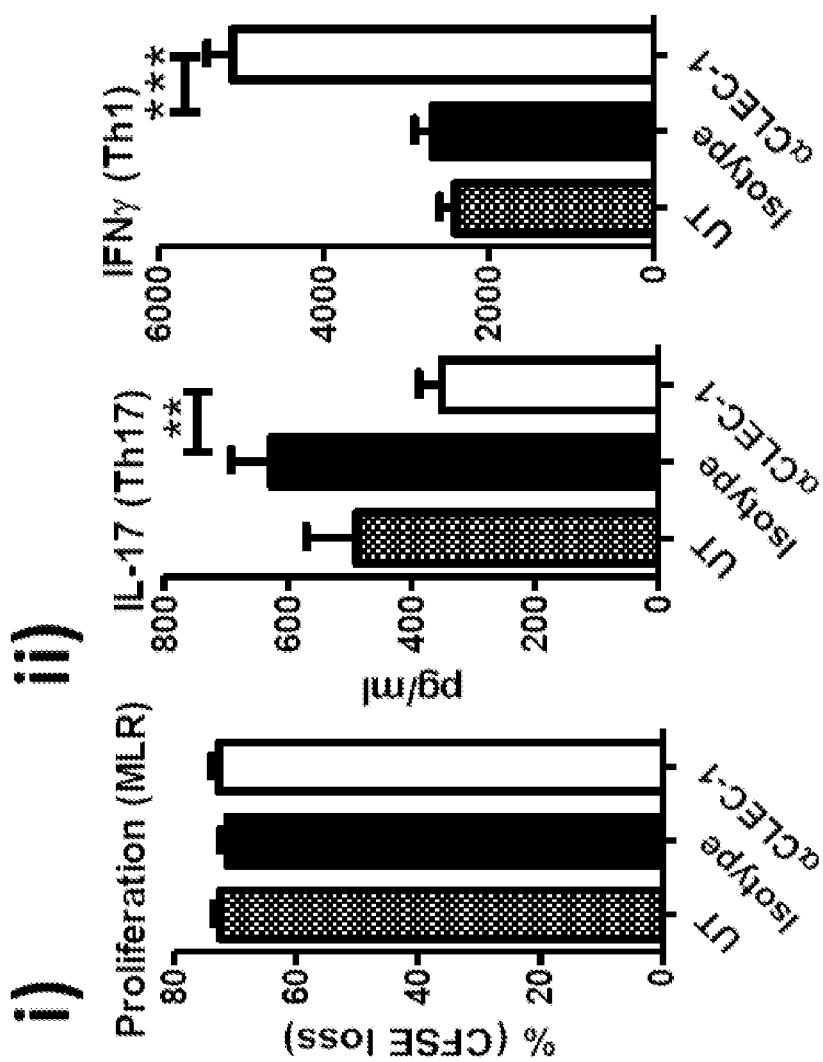

FIG. 2A-C: Effect of CLEC-1 triggering on human moDC maturation and downstream T cell activation.

FIG. 2A) Human moDC incubated with nothing or with plate-bound anti-CLEC-1 mAb or IgG1 isotype control were alternatively stimulated simultaneously with LPS (1 µg/ml) for 24 hours, harvested and CD80, CD86, CD83 and HLA-DR were assessed by flow cytometry and FIG. 2B), TNF-α, IL-12p70, IL-6, IL-23 and IL-10 were assessed in supernatants by ELISA.

FIG. 2C) Then, cells were washed and subjected to MLR with allogeneic T cells for 5 days. Proliferation was assessed by flow cytometry by CFSE dilution in allogeneic T cells and IL-17 and IFN-γ were assessed in supernatant by ELISA.

Figure 3B:
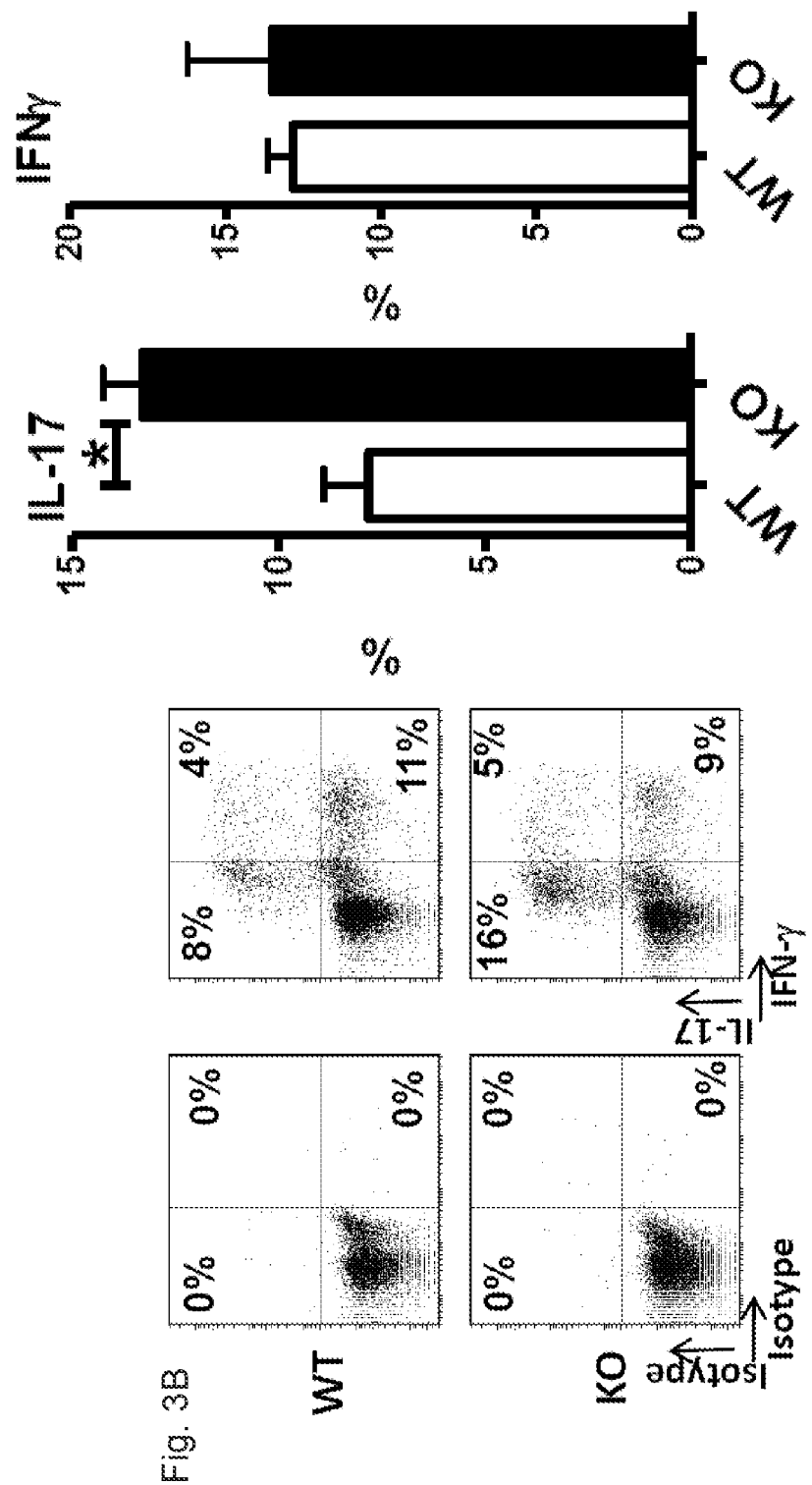

FIG. 3A-B: Effect of CLEC-1 deficiency (CLEC-1 KO rats) on rat BMDC maturation, cytokine secretion and T-cell activation properties.

BMDC were generated from WT or KO rats for 8 days as described in Material and Methods, and incubated for 4 days in MLR with allogeneic purified CD4+ T cells from naïve rats. FIG. 3A Histogram and representative staining of proliferation assessed in CD4+ T cells by CFSE dilution by flow cytometry and FIG. 3B Histogram and representative dot plots of percentage of IL-17+ and IFN-γ+ cells among gated CD4+ T cells assessed by flow cytometry. Data were expressed in histograms as mean±SEM of 4 independent experiments.

Figure 4A:
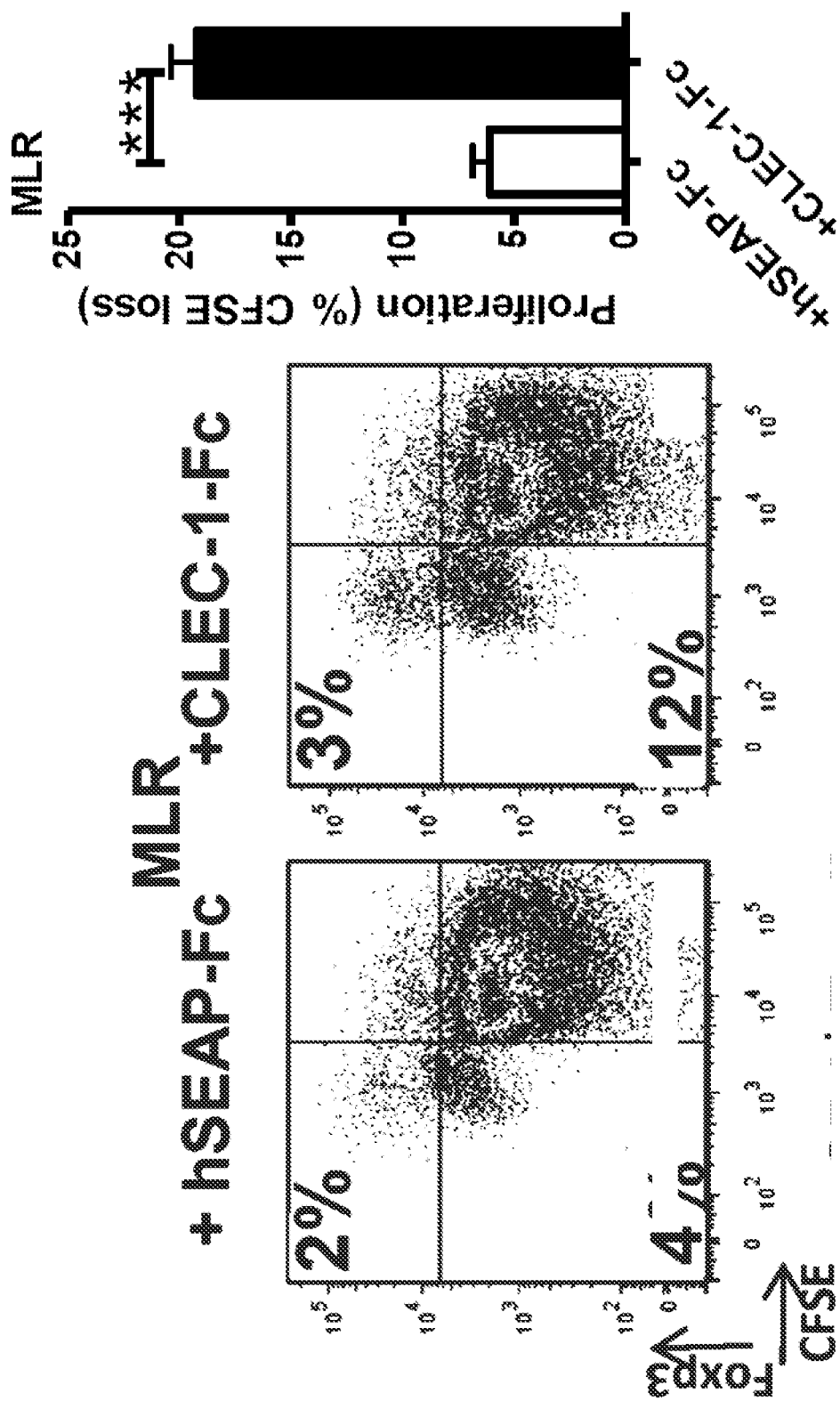
Figure 4B:
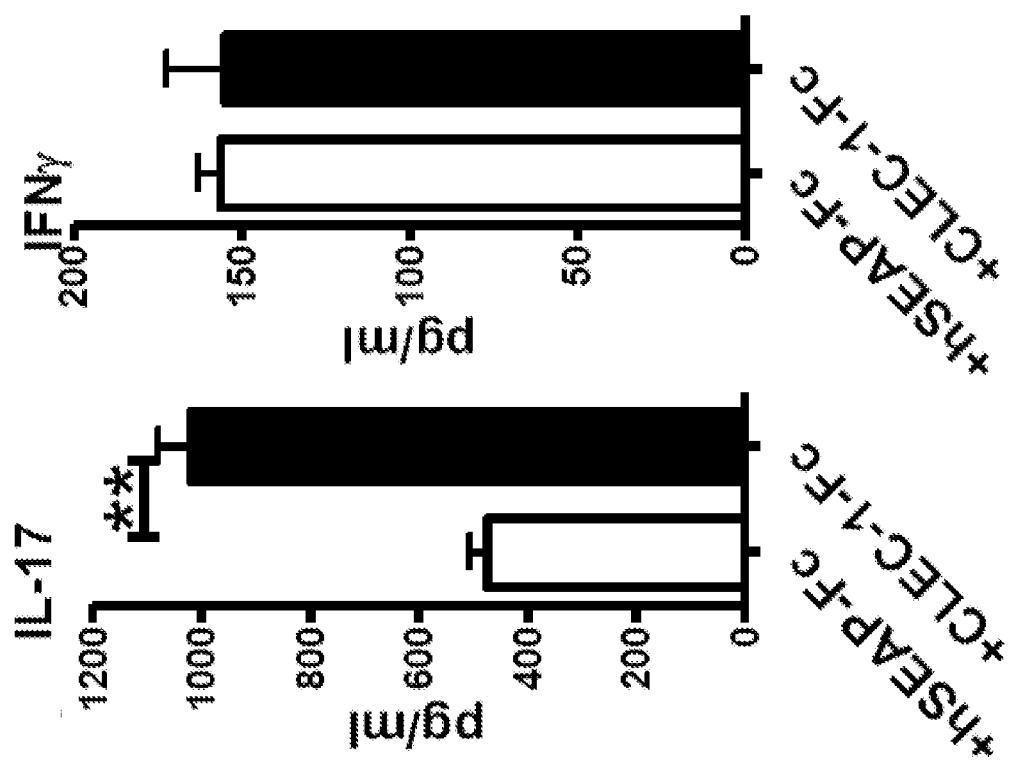

FIG. 4A-B: Effect of CLEC-1 signalling blockade with CLEC-1 Fc fusion protein on rat BMDC-mediated T-cell activation.

BMDCs from WT rats were incubated for 4 days in MLR with allogeneic purified CD4+ T cells from naïve rats together with CLEC-1-Fc or irrelevant hSEAP-Fc fusion proteins (produced and purified under the same conditions) (10 μg/ml). FIG. 4A Proliferation of Foxp3+ and Foxp3− cells were assessed in CD4+ T cells by CFSE dilution by flow cytometry and FIG. 4B IL-17 and IFN-γ cytokine productions were assessed in supernatants of MLR by ELISA. Data were expressed in histograms as mean±SEM of 4 independent experiments.

Figure 5A:
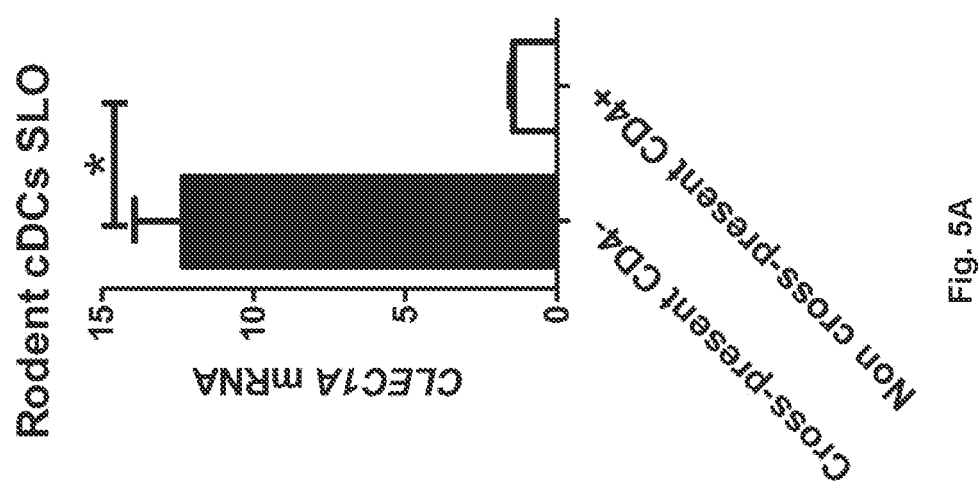
Figure 5B:
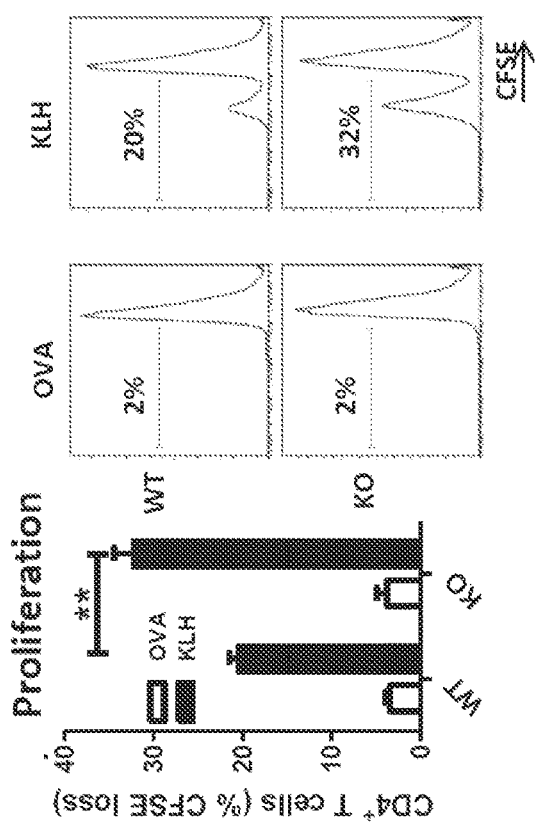
Figure 5B:
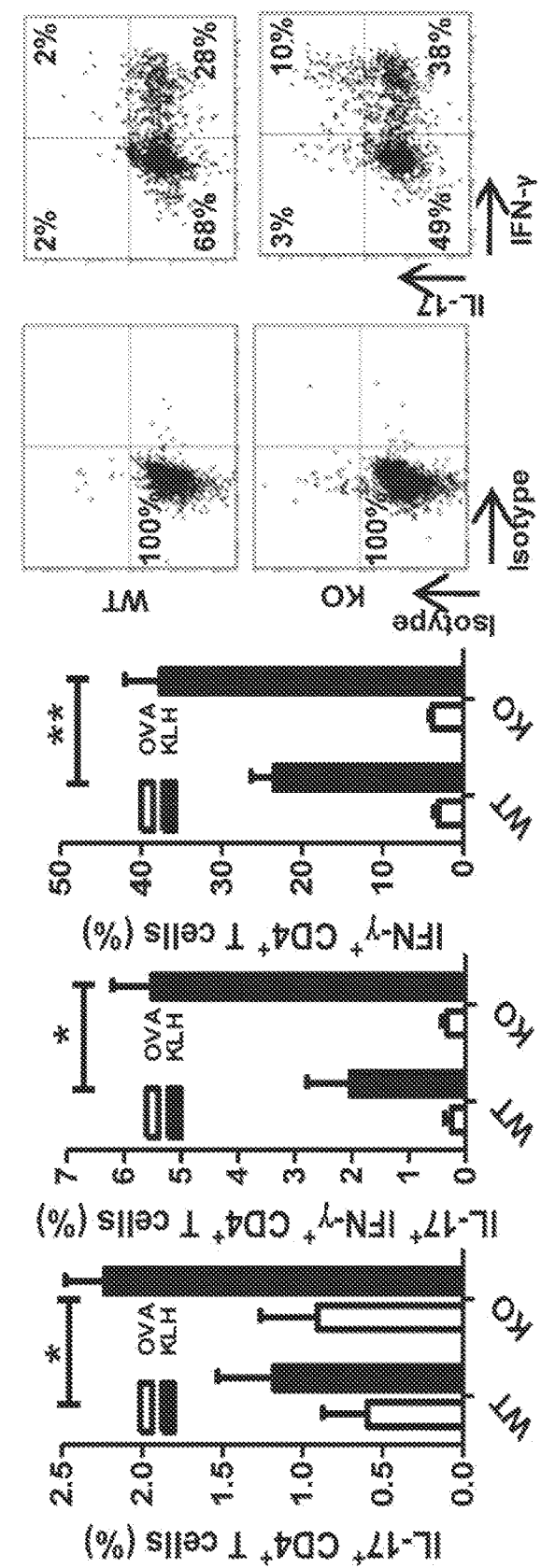

FIG. 5A-B: Effect of CLEC-1 deficiency (CLEC-1 KO rats) on in vivo DC-mediated CD4+ T-cell priming and Th polarization fate.

FIG. 5A) CLEC-1 mRNA expression was assessed by quantitative RT-PCR in different cell subtypes of rat CD103+CD4−(cross-presenting) and CD4+(non-cross-presenting) conventional DCs from secondary lymphoid organs (SLO) (n=5, *p<0.05).

FIG. 5B) WT and CLEC-1 KO rats were immunized subcutaneously in the footpad with CFA plus KLH protein (100 μg/ml). At day 10 after immunization, popliteal lymph nodes were harvested and cultured in the presence of KLH or control OVA (25 μg/ml) for 3 days. Histograms and representative plots of i) Proliferation in CD4+T assessed by CFSE dilution and ii) proportion of IL-17+, IL-17+IFN-γ+ and IFN-γ+ cells among gated CD4+ T cells assessed by flow cytometry. Data were expressed in histograms as mean±SEM of 4 independent experiments.

Figure 6B:
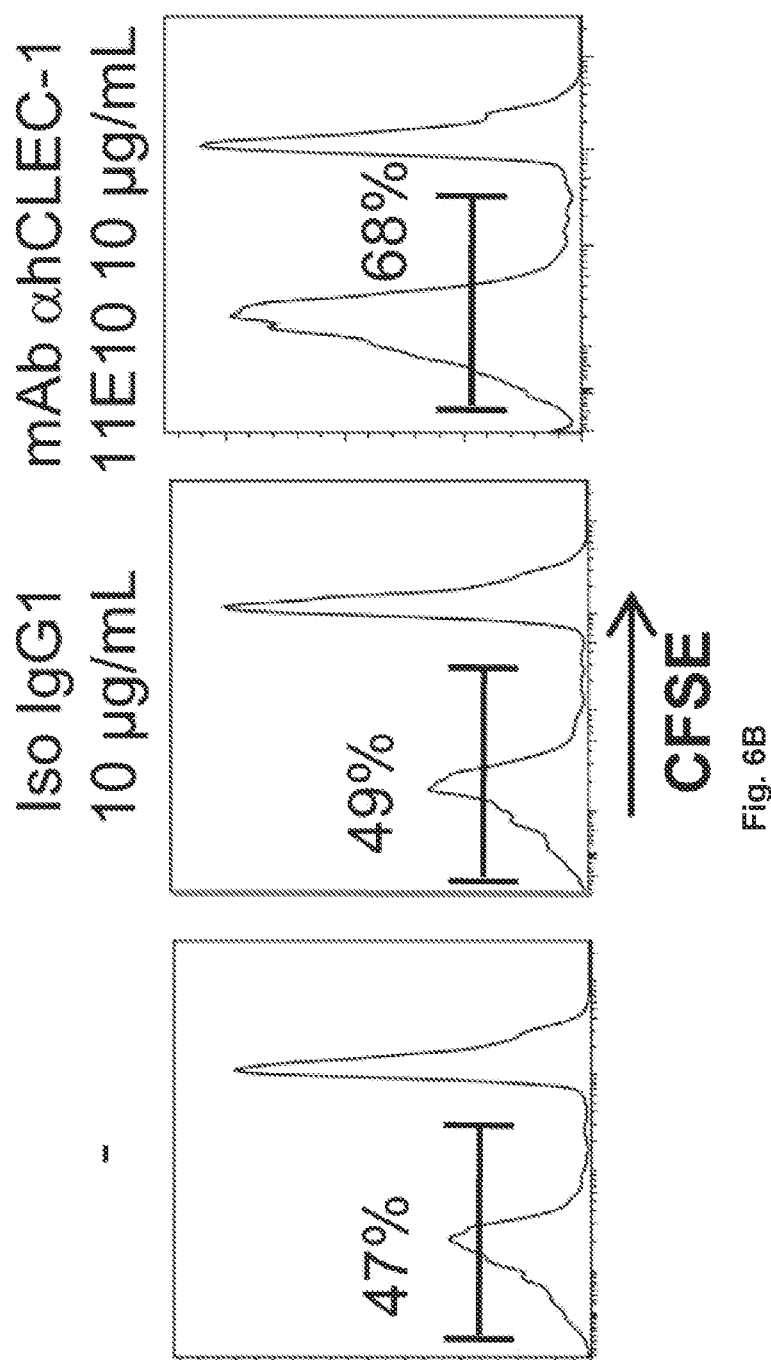
Figure 6C:
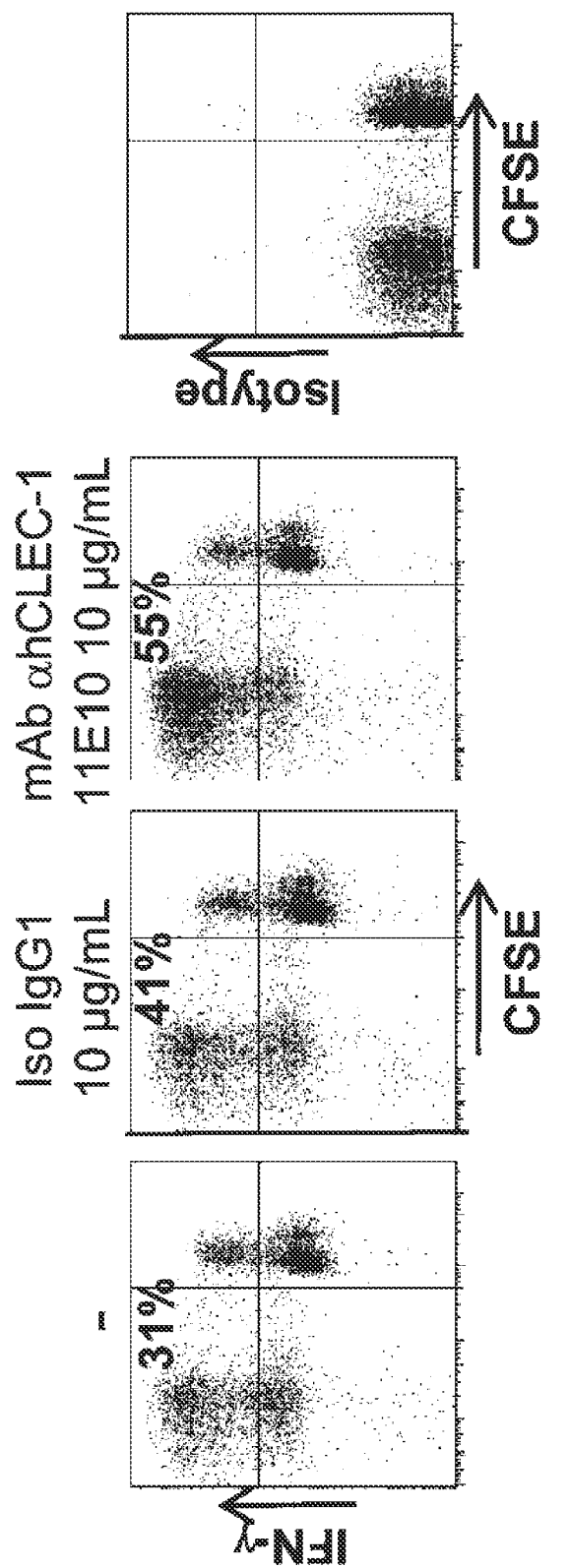

FIG. 6A-C: Effect of potential antagonist of CLEC-1 on MLR activation (moDCs+ Allo T).

MLR was consisted of purified T cells isolated from peripheral blood (5×10$^4$) mixed with allogenic monocytes derived dendritic cells (12.5×103) expressing high level of CLEC-1. Isotype control (IgG1) or anti-human CLEC-1 antibody were added at doses of 0.5 to 10 μg/ml for 5 days. Proliferation of T cells was then assessed by carboxyfluorescein succinimidyl ester dilution and IFN-γ expression assessed by flow cytometry in T cells and by ELISA in supernatants (FIGS. 6A, B and C, histograms and representative plots).

FIG. 7a-d: Inhibitory checkpoint CLEC-1 in cancer (proof of concept in rodent).

FIG. 7a) Rapid and long-lasting expression of CLEC-1 in solid tumors in rodent (hepa 1.6 hepatocarcinoma tumor cells intraportally injected in liver of b6 mice, Clec1a expression was assessed by Q-PCR).

FIG. 7b) CLEC-1 deficient rodents struggle better against tumor than wild-type animals mice: hepa 1.6 hepatocarcinoma tumor cells intraportally injected in liver of b6 WT or Clec1a deficient mice, data are expressed in % of micesurvival Wilcoxson test ***p<0.001

FIG. 7c) rats: C6 glioma cells (1 million) were subcutaneously injected in the flank of sprague dawley (spd) WT or Clec1a deficient rats and tumor volume was monitored until d35.

Figure 7D:
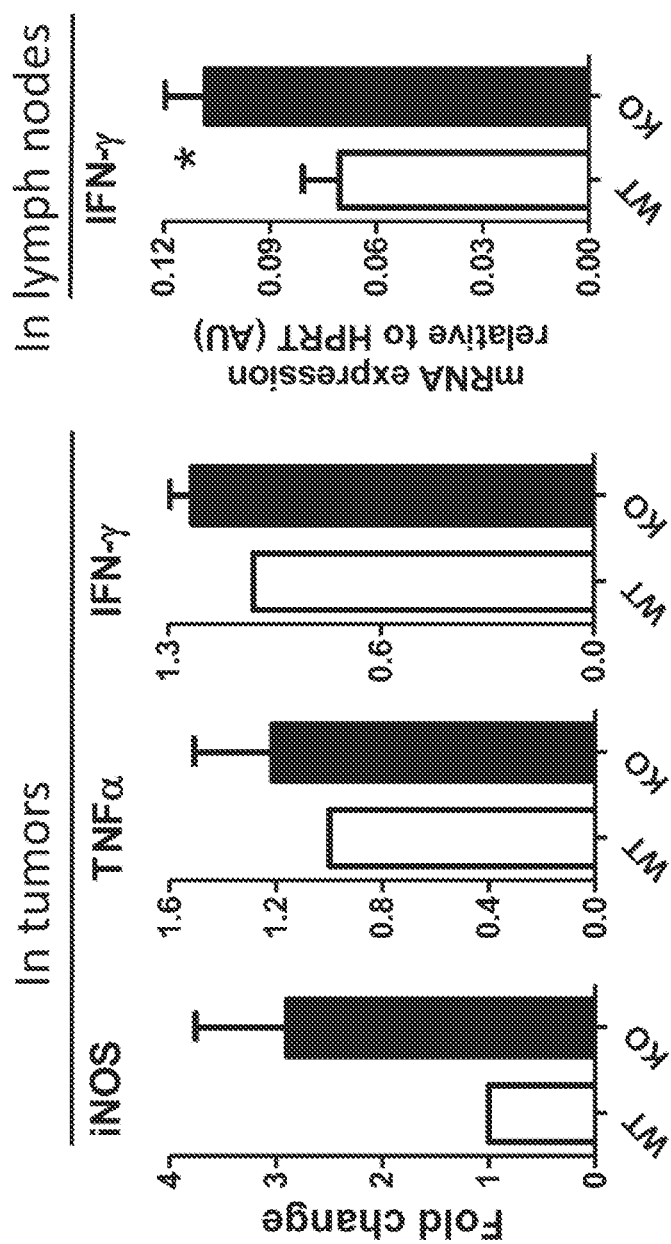

FIG. 7d) C6 glioma cells (1 million) were subcutaneously injected in the flank of sprague dawley (spd) WT or Clec1a deficient rats and tumor and lymph nodes were harvested at day 18 and subjected to Q-PCR for inos, ifng and tnfa. Data represent histograms of expression of inos, ifng and tnfa relative to hprt and expressed in arbitrary unit (fold change compared to the expression in littermate WT rats, value of 1) for tumors (n=3) or in transcrit ratio for lymph nodes (n=6,* p<0.05)

FIG. 8a-d: CLEC-1 is expressed by M2-type pro-tumoral macrophages and is expressed by myeloid cells from pleural effusion mesothelioma and from ovarian tumor ascites.

Figure 8C:
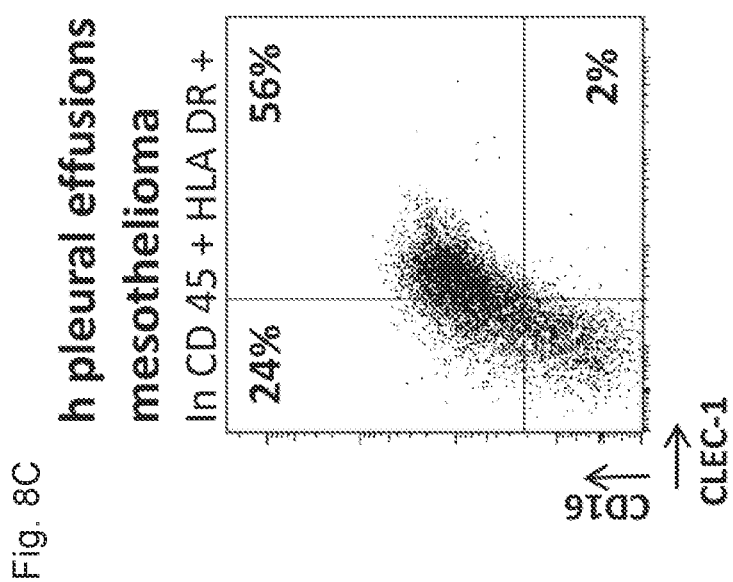

Human monocytes were cultured with M-CSF to generate M0 macrophages and then with IFNγ, LPS or IL-4 to generate M1 or M2 macrophages as described by Zajac, Blood, 2013). CLEC-1 expression was assessed by Q-PCR (FIG. 8a) and by flow cytometry (FIG. 8b), n=4 *p<0.05. Pleural effusion from mesothelioma were collected and subjected to flow cytometry to assess CLEC-1 expression on CD45$^+$ HLA DR$^+$ CD16$^+$ myeloid cells after the blockade of Fc receptors with FcBlock and human AB positive serum (isotype control) (FIG. 8c). Ascites are collected during the routine care of ovarian carcinoma patient and mononuclear cells are isolated after a Ficoll gradient. Human CD14$^+$ cells are isolated using CD14 microbeads and positive selection with AutoMACS. After the blockade of Fc receptors with FcBlock and human AB positive serum, CD14$^+$ cells were stained with either an isotype control monoclonal antibody or an anti-human CLEC-1 (FIG. 8d).

EXAMPLE 1

Material & Methods
Animals

Rats were purchased from the "Centre d'ElevageJanvier" (Genest, Saint-Isle, France) and experimental procedures were carried out in strict accordance with the protocols approved by the Committee on the Ethics of Animal Experiments of Pays de la Loire and authorized by the French Government's Ministry of Higher Education and Research. Clec-1 knock out (KO) were generated by the Transgenic Rats and Immunophenomics Platform facility (SFR-Santé-Nantes) with the zinc finger nucleases (ZFN) technology in the inbred RT1a Lewis background. Absence of CLEC-1 protein at the expected size of 32 kDa was confirmed by western blot.

Antibodies

Anti-human CLEC-1 monoclonal Abs (mAb) was generated by lymphocyte somatic hybridization (Biotem, Apprieu, France) by immunisation of Balb/c mice with a peptide encoding the extracellular domain of hCLEC-1 and selected by screening on recombinant human CLEC-1 protein (RD system) by ELISA and then purified by chromatography on protein A. Anti-human CLEC1 mAb (IgG-D6) was from Santa Cruz Biotechnologies (Dallas, Calif.). Purified anti-rat-β-actin, CD3 (G4.18); anti-rat TCRαβ-A647 or -A488 (R73), CD4-PECy7 (OX35), CD8-A488 (Ox8), IL-17-APC (ebio17B7), Foxp3-APC, IFNγ-FITC, CD11b-

PerCP-Cy5.5 (WT.5), CD103 (αE Integrin)-FITC and anti-human phosphotyrosines (p-Tyr) (4G10), CD4-PE, CD3-APC, CD45-PercP, CD3-FITC, CD19-PE, CD16-PE, CD14-FITC HLA-DR-APC/Cy7, HLA-DR-FITC, CD11c-PECy7, CD11b-FITC CD80-FITC, CD86-FITC, CD83-FITC and IgG1 isotype control were from BD Biosciences (Franklin Lakes).

Generation of Clec-1$^{-/-}$ Knock-Out (KO) Rats by Zinc Finger Nuclease (ZFN) Technology.

In vitro-transcribed mRNA-encoding ZFN-targeted sequences specific for rat clec-1 (Sigma-Aldrich, St Louis, Mo.) were microinjected in fertilized one-cell stage embryos as previously described. Mutations in newborn were detected by PCR. One of the founders that presented a 7 bp deletion leading to a premature stop-codon at the 114 amino-acid of CLEC-1 lacking most of the extracellular domain. Heterozygotes were subjected to breeding to generate KO and wild-type (WT) littermates.

Generation of Rat CLEC-1 Fc Fusion Protein.

The cDNA encoding the extracellular domain of CLEC-1 (ADK94891 amino acids 74-261), was amplified by PCR and the 5' and 3' ends tagged with ECORI BglII restriction sites, respectively. Following digestion, cDNA products were cloned and insert in-frame into pFUSE-mIgG2Ae1-Fc2 v10 [Fab] (Invivogen, San Diego, Calif.) vector containing IgG2a Fc fragment mutated on 3 amino-acid to prevent FcγRI binding. Plasmids were transfected in eukaryote cells with lipofectamine according to the manufacturers' instructions (ThermoFisher). CLEC-1 Fc was purified from supernatant with HiTrap g affinity column (GE Healthcare Bio-sciences, Pittsburgh, Pa.), dialysed using a Slide-A-Lyzer dialysis cassette (ThermoFisher) and quantified using BCA Protein Assay Reagent Kit (Pierce). Purity and protein structure was confirmed by SDS-PAGE followed by Coomassie staining and western blot analysis with anti-mouse IgG or anti-rat CLEC-1 antibody as described in western blot section of supplemental Materials and Methods. A control recombinant secreted truncated form of a human embryonic alkaline phosphatase (hSEAP Fc) was generated (pFUSE-SEAP-hFc, Invivogen) and purified under the same conditions than CLEC-1 Fc.

KLH Immunization

Rats were immunized sc. in the footpad with keyhole limpet hemocyanin (KLH) protein (Sigma) (100 µg) emulsified (v:v) in 100 µl of Complete Freund Adjuvant (CFA) (Difco) and the popliteal lymph nodes were harvested 10 days after immunization. Carboxyfluoresceinsuccinimidyl ester (CFSE) (Molecular Probes/Invitrogen)-labelled (5 µM) total cells ($1 \times 10^5$) or purified CD4$^+$ T cells ($1 \times 10^5$) plus T-cell depleted splenocytes ($1 \times 10^5$) from naïve WT rats were subjected to in vitro secondary challenge with KLH or irrelevant protein OVA (25 µg/ml) for 3 days.

Flow Cytometry and Cell Sorting

Before staining, cells were subjected to Fc block (BD Biosciences) as described by Manufacturer instructions. For intra-cellular cytokine staining, cells were stimulated for 4 hours with PMA and ionomycin (50 ng/ml and 1 µg/ml respectively) in the presence of the protein transport inhibitor GolgiStop (2 µl/well) and subjected to fixation and permeabilization (Facspermeabilizing solution) (all reagents from BD Biosciences). Fluorescent labelling of stained cells (2.5 µg/ml) was measured using a FACS LSR II (BD Biosciences) and analyzed with FlowJo® software (Tree Star, Inc., Ashland).

For cell sorting, rat CD4$^+$ T cells and CD11b$^+$CD103$^+$CD4$^-$ and CD11b$^+$CD103$^+$CD4$^+$ DCs were purified from spleen of naïve rats by positive selection using a FACSAria flow cytometer (BD Biosciences) by TCR$^+$ and CD4$^+$ and by CD11b, CD103 and CD4 staining respectively and for human cells by SSC$^{low}$CD45$^+$CD3$^+$ or CD19$^+$ for T and B cells respectively, SSC$^{high}$CD45$^+$CD16$^+$ for neutrophils, SSC$^{low}$CD45$^+$CD14$^+$ for monocytes and SSC$^{low}$CD45$^+$HLA-DR$^+$CD11c$^+$, for cDCs. Purity was >99%.

Dead cells were excluded by gating on 4',6-diamidino-2-phenylindole (DAPI)-negative cells.

Cells Generation, In Vitro Stimulation and Mixte Leukocyte Reaction (MLR)

Human monocyte-derived DCs (moDCs) were generated from elutriated monocytes cultured for 7 days in complete RPMI 1640 medium (10% endotoxin-free FCS (Perbio Sciences), 2 mM L-glutamine (Sigma), 1 mM sodium pyruvate (Sigma), 1 mMHepes (Sigma), and $5 \times 10^{-5}$ M 2-mercaptoethanol (Sigma)), supplemented with IL-4 (40 ng/ml; AbCys, Paris, France) and GM-CSF (1000 IU/ml; AbCys). Then, cells were stimulated for 24 h ($1 \times 10^6$/ml) with LPS (0.5 µg/ml) (Sigma), Poly I:C (2 µg/ml) (Invivogen, San Diego, Calif.), R848 (2.5 µg/ml) (Invivogen), recombinant human TGFβ1 (20 ng/ml) (R&D systems) alternatively in the presence of 10 µg/ml of anti-CLEC-1 mAb or IgG1 isotype control previously coated to plates) and were subjected to flow cytometry or cultured ($12.5 \times 10^3$) with $5 \times 10^4$ allogeneic human T cells (Pan T Cell Isolation kit (Mylteni)) for 5 days (MLR). Recombinant CLEC-1-His tag (R&D system) or irrelevant recombinant pig alpha1,3GT-6-His proteins were added at 10 µg/ml in MLR. Proliferation was measured by flow cytometry by CFSE profile in CD3$^+$CD4$^+$ cells and IL-17 and IFN-γ cytokines assessed in supernatants by ELISA.

Human endothelial cells (ECs) from aorta (HAEC) or from Umbilical Vein (HUVEC) were isolated and cultured and were alternatively stimulated with 1000 units/ml of recombinant human TNFα (eBiosciences) for 12 hours.

Human monocytes were cultured with M-CSF to generate M0 macrophages and then with IFNγ, LPS or IL-4 to generate M1 or M2 macrophages as described by Zajac, Blood, 2013).

Pleural effusion from patients with mesothelioma were collected and subjected to flow cytometry Ascites are collected during the routine care of ovarian carcinoma patient and mononuclear cells are isolated after a Ficoll gradient. Human CD14$^+$ cells are isolated using CD14 microbeads and positive selection with AutoMACS.

Rat CD4$^+$ T cells were stimulated with plate-bound anti-CD3 (Clone G4.18) (5 µg/ml). Bone Marrow-derived DCs (BMDCs) from naïve, CLEC-1 WT and KO LEW.1A (RT1a) littermates' rats were obtained by culturing cells for 8 days in complete RPMI medium supplemented with rat IL-4 (4 ng/ml) and murine GM-CSF (1.5 ng/ml). Then, BMDCs were stimulated with LPS (1 µg/ml) (Sigma) or zymozan (20 µg/ml) (Invivogen) for 6 hours for transcript analysis and for 24 hours for expression of maturation markers and for MLR (co-culture of 5 days with purified allogeneic CD4$^+$ T cells from mesenteric lymph nodes of LEW.1W (RT1u) naïve rats labelled with 5 µM CFSE). Alternatively, rat CLEC-1 Fc fusion protein and control hSEAP-Fc (10 µg/ml) were added in MLR in the presence of endotoxin inhibitor polymyxine B (10 µg/ml)(Invivogen).

RNA Extraction and Real-Time Quantitative RT-PCR

Total RNA from tissues, tumors or cells was prepared using Trizol (Invitrogen) according to the manufacturer's instructions. cDNA from pooled human organs were from Human Immune System and MTC Panel I from male or female Caucasians (Clontech Mountain View). Real-time quantitative PCR was performed using the ViiA 7 Real-Time PCR System and SYBR® Green PCR Master mix (Applied Biosystems). Hypoxanthine-guanine phosphoribosyltransferase (HPRT) was used as an endogenous control gene to normalize for variations in the starting amount of RNA. Relative expression was calculated using the $2^{-\Delta\Delta Ct}$ method and expressed in arbitrary units.

Immunoprecipitation and Western Blot

Human moDCs were plated on anti-CLEC-1 or control IgG1 isotype (Invitrogen) mAb coated plates (10 µg/ml) for 5 or 20 minutes in medium in conjunction or nor with zymozan (20 µg/ml). Human moDCs, HAEC, HUVEC and HEK were lyzed in Nonidet P-40 1% lysis buffer with protease inhibitors cocktail (Sigma Aldrich). CLEC-1 immunoprecipitation was performed with 4 µg of anti-human CLEC1 mAb (D6) followed by incubation with protein G-Sepharose beads. Proteins were then treated overnight with PNGase F (Sigma Aldrich), eluted and dissolved by boiling for 5 min in Laemmli sample buffer. Protein concentration was determined using the BC assays kit with BSA as standard (Interchim, San Pedro). Nitrocellulose membranes were blocked with Tween-20-Tris buffered saline and 5% milk and incubated with 0.5 µg/ml of antiphosphotyrosine (4G10) or 2 µg/ml of anti CLEC1 mAbs, followed by horseradish peroxidase-conjugated secondary Abs (Jackson immunoresearch, West Grove, Pa.). Proteome Profiler Human NF-κB Pathway Array Kit was performed as described by Manufacturer's instruction (R&D System). Detection by chemiluminescence was performed using West Pico chemiluminescence substrate (Thermofisher scientific, Waltham, Mass.) and protein expression assessed by Las 4000 (Fuji).

Immunohistochemistry

Neutrophils, moDCs, adherent transfected HEK293T cells and HUVEC cells (cultured on a coverslip overnight) were fixed in 4% paraformaldehyde (Electron Microscopy Science, Hatfield, Pa., USA) and permeabilized except for moDCs with Triton ×100 (0.1%). Cells were stained with anti-CLEC1 mAb (D6) or IgG1 isotype control (Invitrogen) (4 µg/ml) for 1 h at room temperature in PBS 1% FCS, 1% BSA and Fc Block for moDCs and then with secondary Alexa Fluor 488 or Alexa Fluor 568 anti-mouse IgG1 antibodies, 1 h. After 10 min incubation in PBS containing 1% DAPI, slides were mounted using Prolong Antifade Reagent (Invitrogen) and observed by fluorescence microscopy (Nikon A1 R Si Confocal microscope). Images were obtained (X60 Plan Apo N.A: 1.4, zoom 2) with sequential mode and analyzed by using ImageJ program.

In Vivo Tumor Models hepa 1.6 hepatocarcinoma tumor cells were intraportally injected in liver of b6 WT or Clec1a deficient mice. C6 glioma cells (1 million) were subcutaneously injected in the flank of sprague dawley (spd) WT or Clec1a deficient rats.

Statistical Analysis

All statistical analyses were performed using Graphpad Prism software (La Jolla) with two-tailed unpaired nonparametric Student's t test (Mann-Whitney). Results were considered significant if p values were <0.05.

Results

Human Myeloid DCs Express CLEC-1 at the Cell-Surface.

Only limited information has been published so far on CLEC-1 expression in human. Very few has been described so far on human CLEC-1 protein expression, regulation and function. There is solely one publication about CLEC-1 expression which discloses that human CLEC-1 could only be detected intracellularly in endothelial cells with a staining pattern resembling endoplasmic reticulum proteins and that neither TGF-β nor inflammatory stimuli could promote significant translocation to the cell surface (The human C-type lectin-like receptor CLEC-1 is upregulated by TGF-β and primarily localized in the endoplasmic membrane compartment. Sattler et al., ScandJImmunol. 2012 March; 75(3): 282-92). Thus, the only information available in the state of the art on hCLEC-1 (ie, intracellular localisation in endothelial cells) is contrary to what was known in the rat (i.e; rCLEC-1 localised on the surface of endothelial and myeloid cells).

The inventors observed by quantitative RT-PCR a strong expression of CLEC-1 transcripts in lung and placenta and a more moderate expression in lymphoid organs such as thymus, lymph nodes, spleen and tonsils (data not shown). In human cell subtypes, abundant CLEC-1 transcripts were found in neutrophils, monocytes, moDCs and HAECs (FIG. 1A) and no transcript was detected in T and B cells. Presence of CLEC-1 protein in moDCs and ECs was confirmed by CLEC-1 immunoprecipitation followed by western blot (data not shown) and contrasts with the low quantity observed in epithelial HEK cells. The inventors generated a mouse anti-human CLEC-1 mAb directed against the extracellular domain and observed a low ectopic expression of CLEC-1 at the cell-surface of transfected HEK cells corroborating what was previously described in the literature (data not shown). As for other CLRs, CLEC-1 may require other adaptor chains, other PRRs or sufficient glycosylation for efficient expression, transport and cell-surface stability. Cell-surface expression of CLEC-1 protein was confirmed by immunohistochemistry in transfected cells (data not shown).

With the generated mAb, they demonstrated by flow cytometry for the first time to our knowledge the cell-surface expression of CLEC-1 on a subpopulation of human blood circulating myeloid CD16$^-$ DCs (CD45$^+$CD14$^-$HLA-DR$^{high}$CD11c$^+$) and on CD14$^+$CD16$^+$ monocytes (CD45$^+$CD14$^+$CD16$^+$). Neither cell-surface expression was observed on BDCA3$^+$ myeloid DC subpopulation (BDCA3$^+$CD45$^+$HLA-DR$^{high}$CD11c$^{low}$) nor on CD123$^+$ plasmacytoid DCs (CD123$^+$CD11c$^-$HLA-DR$^{high}$) (data not shown). Low expression of CLEC-1 was observed at the cell-surface of neutrophils or HAECs for which expression is as previously reported mostly intra-cellular (FIG. 1B). The same localization of CLEC-1 protein was observed by immunohistochemistry with an intra-cellular CLEC-1 staining in human neutrophils and ECs and a cell-surface expression on DCs (data not shown). Importantly, similarly to what we previously described in rat, the inventors observed that CLEC-1 expression in human is down-regulated on DCs by inflammatory stimuli such as TLR ligands and up-regulated by TGFβ (representative dot plots and MFI histogram, FIG. 1C respectively).

CLEC-1 Triggering on Human moDCs Suppresses In Vitro Downstream Allogeneic Th17 Activation.

As CLEC-1 natural ligands have not yet been identified, the inventors used anti-human CLEC-1 mAb to mimic the ligand and cross-link CLEC-1 at the cell-surface of moDCs. Following CLEC-1 immunoprecipitation in low stringent conditions, they observed by western blot no tyrosine phosphorylation at the expected size of CLEC-1 (32 kDa) after CLEC-1 triggering suggesting that tyrosine motif in the cytoplasmic tail is not directly phosphorylated (data not shown). Nevertheless, we observed several changes in tyrosine phosphorylation patterns with enhanced or decreased phosphorylation of several bands around 40-50 kDa in size strongly suggesting that CLEC-1 is a functional receptor that signal via binding partners remaining to be identified.

The inventors then investigated whether CLEC-1 triggering modulates TLR-induced maturation of moDCs as it is described for other activating or inhibitory CLRs. They observed that CLEC-1 triggering neither induces by itself nor potentiates or suppress the LPS-induced maturation state of moDCs according to the expression of the activation markers CD80, CD86, CD83 and HLA-DR (FIG. 2A) and to the production of TNFα, IL-12, IL-6, IL-23 or IL-10 (FIG. 2B). Similar results were observed with other TLR ligands (data not shown).

Then, the inventors evaluated the effect of CLEC-1 triggering on the capacity of moDCs to polarize a downstream allogeneic T cell response. No difference in the subsequent allogeneic T cell proliferation was observed following CLEC-1 triggering alone (FIG. 2C) or in combination with TLRs (data not shown). However, they denoted significantly less of IL-17 and more of IFNγ secreted by allogeneic T cells suggesting that CLEC-1 triggering on moDCs have reduced subsequent allogeneic Th17 activation and skewed the response toward a Th1 one (FIG. 2C).

Given that CLR signaling led to activation of NF-κB, they investigated the level and activation of NF-κB pathway related proteins by Proteome Profiler following CLEC-1 triggering alone or in conjunction with zymosan, an agonist of both DECTIN-1 and TLR signaling pathways. The inventors observed that in contrast to zymozan, CLEC-1 triggering does not induce by itself activation of the NF-κB pathway evaluated by the degradation of the NF-κB inhibitor, IκBα, and by the phosphorylation of the RelA p65 (Ser529) subunit (data not shown). However, they denoted that conjunction of CLEC-1 triggering have reduced the degradation of IκBα induced by zymozan. However, no significant reduction on phosphorylation of the p65 subunit was observed. Since phosphorylation at the Ser529 is IKKβ independent, these data suggest that CLEC-1 may inhibit particularly the IKKβ activation pathway. Collectively, these data suggest that CLEC-1 triggering on human moDCs is functionally active and that although we observed no significant effect on cytokine production, may regulate NF-κB signaling pathways induced by PRRs to finely modulate their activation state and suppress downstream Th17 response.

Disruption of CLEC-1 Signaling in Rat BMDCs Enhances In Vitro T Cell Responses.

To gain insight into the function of CLEC-1, the inventors generated CLEC-1 deficient rats. CLEC-1 deficient rats were viable, healthy and were born from heterozygote breeding with the expected Mendelian frequency. At steady-state, CLEC-1 deficient rats exhibited regular myeloid and lymphoid immune cell compartments in blood and peripheral lymphoid organs (data not shown).

The inventors generated BMDCs from CLEC-1 deficient rats and observed that these cells differentiate and maturate normally in response to LPS stimulation (CD80, CD86, Class I and II MHC) (data not shown). Interestingly, they observed that following activation by LPS or zymosan, CLEC-1 deficient BMDCs expressed higher level of IL-12p40 transcripts than BMDCs from wild-type rats (data not shown). No significant difference was observed for IL-6, IL-23, TGFβ and IL-10 expression. However, impressively, CLEC-1 deficient BMDCs induced an enhanced proliferation of allogeneic CD4$^+$ T cells that was associated with an increased activation of Th17 T cells (FIG. 3).

To further confirm these data, the inventors generated rat CLEC-1 Fc fusion protein (data not shown). This fusion protein consisted of the extracellular domain of rat CLEC-1 fused to IgG Fc fragment mutated on 3 amino-acid to prevent FcγRI binding, should block CLEC-1 interactions on BMDCs with its putative ligands and thus mimic CLEC-1 deficiency. Similarly, they observed in the presence of CLEC-1 Fc fusion protein in the in vitro MLR, a more prominent proliferation of non-Foxp3 allogeneic effector T cells and more Th17 activation (FIG. 4). Importantly, no induction of Th-17 was observed with CLEC-1 Fc on purified T cells following anti-CD3 polyclonal activation (data not shown) demonstrating that this effect was specific to CLEC-1 signaling disruption in BMDCs and not due to ligation of CLEC-1 Fc and agonist effect on a putative ligand on T cells.

Taken collectively, these data suggest that the absence of CLEC-1 signaling in myeloid cells, notably in DCs enhanced their activation state required for in vitro efficient T cell proliferation and activation.

CLEC-1 Deficiency Enhances In Vivo DC-Mediated T Cell Response.

The inventors then investigated the potential function of CLEC-1 in vivo in DC-mediated Th differentiation following immunization by subcutaneous injection with the foreign antigen keyhole limpet hemocyanin (KLH) and complete Freund adjuvant. First, they evaluated CLEC-1 transcripts expression in different subtypes of cDCs CD103$^+$ CD11b$^+$ in lymph nodes. Interestingly, they observed that CLEC-1 expression is restricted to CD4$^-$ DCs corresponding to CD8α$^+$ DC in mice specialized for the phagocytosis of dead cells and that exhibit cytotoxic activity (FIG. 5A).

Following immunization, they observed after in vitro secondary challenge of draining lymph node, an increased proliferation of KLH-specific CD4$^+$ T cells from immunized CLEC-1 deficient rats that was associated with an increased number of IL-17$^+$, IL-17$^+$IFNγ$^+$ and IFNγ$^+$ CD4$^+$ T cells (histogram and representative dot plots, FIG. 5B). Importantly, enhanced recall response to KLH was also observed with purified CD4$^+$ T cells from immunized CLEC-1 deficient rats in the presence of DCs from wild-type rats demonstrating a specific increase in the in vivo T cell priming in the absence of CLEC-1 (data not shown).

These data demonstrate in vivo that the deficiency of CLEC-1 signaling in cDCs exacerbates downstream T cell-mediated immune response.

DISCUSSION

In this study, the inventors demonstrated for the first time to our knowledge, that human CLEC-1 is a functional DC cell-surface regulatory receptor that suppresses subsequent effector Th17 response. Moreover, CLEC-1 deficient rats revealed an in vivo role for CLEC-1 in prevention of excessive DC-mediated CD4$^+$ T cell priming. As in rat, they observed that CLEC-1 expression in human moDCs is decreased by inflammatory stimuli and is up-regulated by TGFβ. This profile of expression in DCs with a decrease following inflammatory stimulation represents a classic response observed for other inhibitory receptors such as MICL or DCIR that have also been shown to suppress in vivo T cell responses and inflammation (Uto T. et al. Clec4A4 is a regulatory receptor for dendritic cells that impairs inflammation and T-cell immunity. Nat Commun. 2016; 7:11273) (Redelinghuys P, et al. MICL controls inflammation in rheumatoid arthritis. Ann Rheum Dis. 2015). Interestingly, the inventors found that CLEC-1 is expressed in rat by the CD4$^+$ subpopulation of cDCs in lymphoid organs. This subpopulation of DCs correspond to CD8α$^+$ DCs mice counterparts involved in cytotoxic activity and phagocytosis of dead cells and that is described to be the main producers of IL-12 and involved in cross-presentation of tumor antigens. This pattern of expression contrast with the inhibitory receptor DCIR-2 that has been shown to be restricted to CD8α⁻cDCs. Nevertheless, in human blood, CLEC-1 was observed to be expressed at cell-surface on a subpopulation of CD16⁻CD14⁻ myeloid DCs and not on BDCA3⁺ DCs, the human counterparts of CD8α⁺ DCs. This discrepancy between human and rodent warrants further investigation. The inventors observed that disruption of CLEC-1 signaling enhances particularly DC-mediated Th17 activation in vitro but both Th1 and Th17 responses were increased following immunization in vivo. This suggests that CLEC-1 may differently suppress Th1 and Th17 responses according to co-engagement of PRRs. Conversely, DECTIN-1 that acts as an activating receptor in DCs, differently promotes the Th17/Th1 balance according to the ligands and PRR co-engagement by finely regulating the secretion of the polarizing cytokines IL-12 and IL-23 (Gringhuis S I, et al. Dectin-1 directs T helper cell differentiation by controlling noncanonical NF-kappaB activation through Raf-1 and Syk. Nat Immunol. 2009; 10(2):203-213) (LeibundGut-Landmann S, et al. Syk- and CARDS-dependent coupling of innate immunity to the induction of T helper cells that produce interleukin 17. Nat Immunol. 2007; 8(6):630-638) (Lee E J, et al. Mincle Activation and the Syk/Card9 Signaling Axis Are Central to the Development of Autoimmune Disease of the Eye. J Immunol. 2016; 196(7):3148-3158). For example, in response to *Aspergillus Fumigatus* challenge, DECTIN-1 was shown in mice to potentiate Th17 differentiation notably by decreasing IFN-γ and IL12p40 expression thereby decreasing Th1 polarization. Intriguingly, the inventors did not observe that CLEC-1 signaling in DCs suppress the PRR-induced expression of Th17 polarizing cytokines and noted only an effect on IL-12p40 production on rat KO BMDCs. These results suggest that CLEC-1 in DCs may shape the Th17/Th1 balance by other mechanisms than the expression of polarizing cytokines. For example, DECTIN-1 signaling has been shown to influence T cell polarization fate by also modulating the expression of the costimulatory molecules Ox40 ligand on DCs (Joo H, et al. Opposing Roles of Dectin-1 Expressed on Human Plasmacytoid Dendritic Cells and Myeloid Dendritic Cells in Th2 Polarization. J Immunol. 2015; 195(4):1723-1731). Interestingly, the inventors observed that CLEC-1 triggering on human DCs prevent the IκBα degradation induced by DECTIN-1 signaling. Therefore, CLEC-1 may also prevent the Card9 signaling pathway mediated by activating CLRs and known to specifically sustain Th17 response.

They have not been able to detect with CLEC-1 Fc fusion protein the cells expressing endogenous ligands. Nevertheless, their data suggest that CLEC-1 ligands may be expressed by hematopoietic cells or released "naturally" or in particular context of tissue or cell damage. Ligands may be expressed by the CLEC-1 expressing cells themselves as it is the case for DCIR-2 or alternatively on T cells. Endogenous DECTIN-1 ligand has been reported to be expressed by T cells that in contrast to CLEC-1 acts as a costimulatory molecule enhancing T cell proliferation (Ariizumi K, et al. Identification of a novel, dendritic cell-associated molecule, dectin-1, by subtractive cDNA cloning. J Biol Chem. 2000; 275(26):20157-20167).

These findings establish the relevance of CLEC-1 in DCs in the tight control of the degree and quality of downstream T cell activation and as a cell-surface receptor may provide a therapeutic tool to manipulate T cell response.

Therefore, CLEC-1 as a cell-surface inhibitory receptor in myeloid cells highlights a potential target for therapeutic intervention and new treatment paradigm in cancer.

Several experimental studies demonstrate that CLRs contribute to cancer progression and metastatic spread by their function in cell-adhesion or in T-cell response shaping ((Yan, Kamiya et al. 2015; Ding, Yao et al. 2017). For example, the immunomodulatory receptors DC-SIGN, MINCLE, DCIR and BDCA-2 have been shown to inhibit myeloid cell activation, inflammation and be critical to drive Foxp3⁺ CD4⁺ CD25⁺ Tregs expansion (Yan, Kamiya et al. 2015; Ding, Yao et al. 2017). DC-SIGN recognize carcinoembryonic antigen overexpressed on almost all human carcinoma (Nonaka, Ma et al. 2008) and promotes the secretion of the immunosuppressive cytokines IL-10 and IL-6 by myeloid cells. Besides, polymorphisms in DC-SIGN gene promoter were found to be associated with increased risk in colorectal cancer patients (Lu, Bevier et al. 2013). MINCLE was shown to be enhanced in tumor infiltrating leukocytes in pancreatic ductal adenocarcinoma and especially by myeloid suppressive cells (MSCs). Ligation of MINCLE with SAP130 (a subunit of the histone deacetylase complex) released from dying cells induces strong peritumoral suppression (Seifert, Werba et al. 2016). Similarly, the CLR LOX-1 has been shown to be specifically enhanced at the cell surface of blood or tumor-infiltrating neutrophils (15 to 50%) in cancer patients whereas is nearly undetectable in blood of healthy donors (Condamine, Dominguez et al. 2016). In this study, they showed that endoplasmic reticulum stress induces LOX-1 expression and convert neutrophils to MSCs with strong suppressive function.

Conversely, triggering signaling of activating CLR such as DECTIN-1, has been shown to mount anti-tumor immunity and to decrease Tregs and MSCs (Tian, Ma et al. 2013). Administration of beta-glucans, a ligand of DECTIN-1 inhibits tumor growth in murine carcinoma models (Li, Cai et al. 2010; Masuda, Inoue et al. 2013; Tian, Ma et al. 2013), in human melanoma, neuroblastoma, lymphoma xenograft models (Modak, Koehne et al. 2005) as well as in human ovarian and gastric cancer (Inoue, Tanaka et al. 1993; Oba, Kobayashi et al. 2009).

Therefore, enhancing DC or more broadly myeloid cell activation by CLEC-1 antagonist may represent an immune checkpoint target to modulate downstream effector T-cell immune that could have important clinical implication in cancer.

EXAMPLE 2

The inventors previously showed in rat that CLEC-1 blockade with CLEC-1 Fc fusion protein enhance T cell proliferation in a mixed leukocyte reaction (MLR) (see EXAMPLE 1). They have generated several mAbs directed against the extra-cellular part of human CLEC-1 and they show that one mAbs appears antagonist of CLEC-1 signalling and thus enhances T cell proliferation and IFN-γ production in mixte leukocyte reaction (MLR). MLR was consisted of purified T cells isolated from peripheral blood ($5 \times 10^4$) mixed with allogenic monocytes derived dendritic cells ($12.5 \times 10^3$) expressing high level of CLEC-1. Isotype control (IgG1) or anti-human CLEC-1 antibody were added at doses of 0.5 to 10 μg/ml for 5 days. Proliferation of T cells was then assessed by carboxyfluorescein succinimidyl ester dilution and IFNγ expression assessed by flow cytometry in T cells and by ELISA in supernatants (FIGS. 6A and 6B, 6C histograms and representative plots).

EXAMPLE 3

CLEC-1 is Highly Expressed in Tumors and Plays a Functional Role in Tumor Immunity In a mouse hepatocarcinoma model (intraportal injection of hepa 1.6 tumor cells), the inventors observed an increased and long-lasting expression of CLEC-1 in tumors (FIG. 7a). Importantly, in this model, mice deficient in CLEC-1 (kindly gifted by Derrick J. Rossi, Harvard Stem Cell Institute, Cambridge) are better resistant to tumor growth and exhibit an increased survival rate (median survival 28 d in KO versus 21 d in WT) (FIG. 7b). Similarly, in a subcutaneous (sc.) rat glioma model (C6), the inventors observed total regression of tumors in 3 out of 5 of CLEC-1 deficient rats (generated by ZFN technology in our lab) (FIG. 7c). Importantly, by Q-PCR in tumors harvested at day 18 after tumor cell inoculation, a higher mRNA expression of inos, tnfa and ifng were assessed in tumor from CLEC-1 deficient rats (FIG. 7d). In addition, a higher mRNA expression of ifng was detected in lymph nodes (FIG. 7d). These data demonstrate a better anti-tumor response in CLEC-1 deficient rats and suggest that the absence of CLEC1 have induced more anti-tumoral M1 macrophages and more cytotoxic and Th1 T cells.

CLEC-1 Expression is Restricted to cDCs Specialized in Cross Presentation

Interestingly, the inventors observed in both rat and mice that CLEC-1 expression by cDCs from secondary lymphoid organs is restricted to the specific subset of DCs specialized in the cross presentation of antigens (CD4+ in rat, CD8α+ in mice) (FIG. 5A). These cells were shown to secrete high level of IL-12 and to be responsible for the activation of anti-tumor cytotoxicCD8+ T lymphocyte (CTL) response. Therefore, by acting as an inhibitory receptor in the specialized subsets of DCs, CLEC-1 triggering may prevent IL-12 production, efficient cross presentation and CTL response towards tumor antigens.

CLEC-1 is Expressed by M2-Type Pro-Tumoral Macrophages and is Expressed by Myeloid Cells from Pleural Effusion Mesothelioma and from Ovarian Tumor Ascites.

The inventors observed higher CLEC-1 expression at both transcripts (a) and protein level (b) on human M2-type protumoral macrophages compared to M1-type anti-tumoral macrophages or compared to M0 macrophages (FIG. 8). Furthermore, they observed CLEC-1 cell-surface protein expression on human myeloid CD45+ HLADR+ CD16+ cells from pleural effusion mesothelioma (c) and on CD14+ myeloid cells from ovarian carcinoma ascites (d) compared to control isotype (FIG. 8). These data demonstrate that CLEC-1 expression is enhanced on myeloid cells in tumor microenvironment and could play a critical role in tumor immune escape.

In conclusion, in view of the results above (in particular results showing that CLEC-1 Fc fusion protein and antibodies directed against the extra-cellular part of human CLEC-1 enhance T cell proliferation), it appears credible that CLEC-1 antagonists may be used for the treatment of cancer.

REFERENCES

Throughout this application, various references describe the state of the art to which this invention pertains. The disclosures of these references are hereby incorporated by reference into the present disclosure.

---

The invention claimed is:

1. A method of promoting T cells response in a human subject suffering from cancer, comprising administering to the subject a therapeutically effective amount of an antagonist of human CLEC-1, wherein the antagonist is selected from the group consisting of an antibody, an antigen-binding fragment thereof, and a polypeptide that is a functional equivalent of human CLEC-1 having at least 90% identity with the amino acid sequence set forth in SEQ ID NO: 1.

2. The method of claim 1 wherein the subject suffers from a cancer selected from the group consisting of bile duct cancer, bladder cancer, bone cancer, brain and central nervous system cancer, breast cancer, Castleman disease cervical cancer, colorectal cancer, endometrial cancer, esophagus cancer, gallbladder cancer, gastrointestinal carcinoid tumors, Hodgkin's disease, non-Hodgkin's lymphoma, Kaposi's sarcoma, kidney cancer, laryngeal and hypopharyngeal cancer, liver cancer, lung cancer, mesothelioma, plasmacytoma, nasal cavity and paranasal sinus cancer, nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma, salivary gland cancer, skin cancer, stomach cancer, testicular cancer, thymus cancer, thyroid cancer, vaginal cancer, vulvar cancer, and uterine cancer.

3. The method of claim 1, wherein the antibody or antigen-binding fragment is selected from the group consisting of chimeric antibodies, humanized antibodies and fully human monoclonal antibodies.

4. The method of claim 1, wherein the antibody or antigen-binding fragment thereof specifically binds to the extracellular domain of human CLEC-1.

5. The method according to claim 1, wherein the polypeptide that is a functional equivalent of human CLEC-1 is fused to an immunoglobulin constant domain.

6. The method according to claim 1, wherein the antagonist of human CLEC-1 is used in combination with a conventional treatment.

7. The method according to according to claim 1, wherein the antagonist of human CLEC-1 is used in combination with a chemotherapeutic agent, a targeted cancer therapy, an immunotherapeutic agent or radiotherapy.

8. A method of treating cancer by promoting a T cell response, in a subject in need thereof, comprising administering to the subject a therapeutically effective amount of an antagonist of human CLEC-1 selected from the group consisting of an antibody, an antigen-binding fragment thereof, and a polypeptide that is a functional equivalent of human CLEC-1 having at least 90% identity with the amino acid sequence set forth in SEQ ID NO: 1.

9. The method according to claim 8, wherein the antagonist of human CLEC-1 is used in combination with a conventional treatment.

10. The method according to according to claim 8, wherein the antagonist of human CLEC-1 is used in combination with a chemotherapeutic agent, a targeted cancer therapy, an immunotherapeutic agent or radiotherapy.

* * * * *

SEQUENCE LISTING

<160> NUMBER OF SEQ ID NOS: 2

<210> SEQ ID NO 1
<211> LENGTH: 206
<212> TYPE: PRT
<213> ORGANISM: Artificial Sequence
<220> FEATURE:
<223> OTHER INFORMATION: synthesized

<400> SEQUENCE: 1

```
Tyr Tyr Gln Leu Ser Asn Thr Gly Gln Asp Thr Ile Ser Gln Met Glu
1               5                   10                  15

Glu Arg Leu Gly Asn Thr Ser Gln Glu Leu Gln Ser Leu Gln Val Gln
            20                  25                  30

Asn Ile Lys Leu Ala Gly Ser Leu Gln His Val Ala Glu Lys Leu Cys
        35                  40                  45

Arg Glu Leu Tyr Asn Lys Ala Gly Ala His Arg Cys Ser Pro Cys Thr
    50                  55                  60

Glu Gln Trp Lys Trp His Gly Asp Asn Cys Tyr Gln Phe Tyr Lys Asp
65                  70                  75                  80

Ser Lys Ser Trp Glu Asp Cys Lys Tyr Phe Cys Leu Ser Glu Asn Ser
                85                  90                  95

Thr Met Leu Lys Ile Asn Lys Gln Glu Asp Leu Glu Phe Ala Ala Ser
            100                 105                 110

Gln Ser Tyr Ser Glu Phe Phe Tyr Ser Tyr Trp Thr Gly Leu Leu Arg
        115                 120                 125
```

-continued

```
Pro Asp Ser Gly Lys Ala Trp Leu Trp Met Asp Gly Thr Pro Phe Thr
    130                 135             140
Ser Glu Leu Phe His Ile Ile Ile Asp Val Thr Ser Pro Arg Ser Arg
145                 150                 155                 160
Asp Cys Val Ala Ile Leu Asn Gly Met Ile Phe Ser Lys Asp Cys Lys
                165                 170                 175
Glu Leu Lys Arg Cys Val Cys Glu Arg Arg Ala Gly Met Val Lys Pro
            180                 185                 190
Glu Ser Leu His Val Pro Pro Glu Thr Leu Gly Glu Gly Asp
        195                 200                 205

<210> SEQ ID NO 2
<211> LENGTH: 24
<212> TYPE: PRT
<213> ORGANISM: Artificial Sequence
<220> FEATURE:
<223> OTHER INFORMATION: synthesized

<400> SEQUENCE: 2

Cys Glu Arg Arg Ala Gly Met Val Lys Pro Glu Ser Leu His Val Pro
1               5                   10                  15
Pro Glu Thr Leu Gly Glu Gly Asp
            20
```